(12) United States Patent
Kumamoto et al.

(10) Patent No.: US 9,707,551 B2
(45) Date of Patent: Jul. 18, 2017

(54) REACTION CATALYST FOR CROSS-COUPLING AND METHOD FOR MANUFACTURING AROMATIC COMPOUND

(71) Applicant: HOKKO CHEMICAL INDUSTRY CO., LTD., Chuo-ku, Tokyo (JP)

(72) Inventors: Nobumichi Kumamoto, Atsugi (JP); Kenta Suzuki, Atsugi (JP)

(73) Assignee: HOKKO CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/762,456

(22) PCT Filed: Jan. 23, 2014

(86) PCT No.: PCT/JP2014/051398
§ 371 (c)(1),
(2) Date: Jul. 21, 2015

(87) PCT Pub. No.: WO2014/115813
PCT Pub. Date: Jul. 31, 2014

(65) Prior Publication Data
US 2015/0360214 A1 Dec. 17, 2015

(30) Foreign Application Priority Data

Jan. 23, 2013 (JP) ................... 2013-010552

(51) Int. Cl.
| | |
|---|---|
| *C07D 209/82* | (2006.01) |
| *C07C 209/10* | (2006.01) |
| *B01J 31/24* | (2006.01) |
| *C07D 295/02* | (2006.01) |
| *C07F 9/50* | (2006.01) |
| *C07F 9/54* | (2006.01) |
| *C07C 1/32* | (2006.01) |
| *C07C 41/30* | (2006.01) |
| *C07C 253/30* | (2006.01) |
| *C07D 295/033* | (2006.01) |

(52) U.S. Cl.
CPC ............ *B01J 31/24* (2013.01); *C07C 1/321* (2013.01); *C07C 41/30* (2013.01); *C07C 209/10* (2013.01); *C07C 253/30* (2013.01); *C07D 209/82* (2013.01); *C07D 295/02* (2013.01); *C07D 295/033* (2013.01); *C07F 9/5013* (2013.01); *C07F 9/5428* (2013.01); *B01J 2231/4283* (2013.01); *B01J 2531/824* (2013.01); *C07C 2531/24* (2013.01)

(58) Field of Classification Search
CPC ...................... C07D 209/82; C07C 209/10
See application file for complete search history.

(56) References Cited

U.S. PATENT DOCUMENTS 5,576,460 A 11/1996 Buchwald et al.

FOREIGN PATENT DOCUMENTS

| | | |
|---|---|---|
| CN | 101195641 A1 | 6/2008 |
| EP | 0539677 A | 5/1993 |
| JP | 859514 A | 3/1996 |
| JP | 2002506836 A | 3/2002 |
| JP | 2002520328 A | 7/2002 |
| JP | 2004537405 A | 12/2004 |
| JP | 2009298773 A | 12/2009 |

(Continued)

OTHER PUBLICATIONS

Notification Concerning Transmittal of International Preliminary Report on Patentability (PCT/IB326) and Notification of Transmittal of Translation of the International Preliminary Report on Patentability (PCT/IB/338) mailed Aug. 6, 2015, with with International Preliminary Report on Patentability (PCT/IB/373) and Written Opinion of the International Searching Authority (PCT/ISA/237), for corresponding international application PCT/JP2014/051398.

Anil S. Guram et al., New Catalysts for Suzuki-Miyaura Coupling Reactions of Heteroatom-Substituted Heteroaryl Chlorides, The Journal of Organic Chemistry, Feb. 19, 2007, p. 5104-5112, vol. 72, American Chemical Society.

Bosch,M. et al., A Series of (Butadiene)rhodium (I) Complexes with an Open-Sandwich- or HalfSandwich-Type Structure, Chemistry—A European Journal, 1999, vol. 5, No. 7, p. 2203-2211.

(Continued)

*Primary Examiner* — Shawquia Jackson
(74) *Attorney, Agent, or Firm* — Law Office of Katsuhiro Arai

(57) ABSTRACT

The object of the present invention is to provide a new organic phosphorus ligand that can efficiently promote cross-coupling reaction to obtain the target substance at high yield, as well as a method of manufacturing such ligand whose steric characteristics and electronic characteristics can be fine-tuned and which can be used to cause cross-coupling reaction at high yield. As a means for achieving the aforementioned object, a phosphine compound expressed by General Formula (1) below is provided.

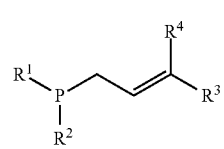

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time).

6 Claims, No Drawings

(56) References Cited

FOREIGN PATENT DOCUMENTS

| WO | 9947474 A1 | 9/1999 |
| WO | 0002887 A2 | 1/2000 |
| WO | 03013723 A1 | 2/2003 |

OTHER PUBLICATIONS

Crocker,C. et al., Large-ring and cyclometalated rhodium complexes from some medium-chain ~,w.-diphosphines, Journal of the American Chemical Society, 1980, vol. 102, No. 13, p. 4373-4379.

International Search Report (ISR) mailed Apr. 15, 2014, issued for International application No. PCT/JP2014/051398.

Miyaura, Norio; Suzuki, Akira, Palladium-Catalyzed Cross-Coupling Reactions of Organoboron Compounds, Chemical reviews, Aug. 17, 1996, 95(7), p. 2457-2483, American Chemical Society.

A First Office Action with search report issued by the State Intellectual Property Office of China on May 20, 2016 for Chinese counterpart application No. 201480005612.8.

Butti et al., Palladium-Catalyzed Enantioselective Allylic Phosphination, Angew.Chem.Int.Ed, Dec. 31, 2008, 4878-4881, vol. 47.

Extended European Search Report (EESR) dated Jul. 11, 2016, issued for European counterpart patent application No. EP14743668.

REACTION CATALYST FOR CROSS-COUPLING AND METHOD FOR MANUFACTURING AROMATIC COMPOUND

This application is the U.S. National Phase under 35 U.S.C. §371 of International Application PCT/JP2014/051398, filed Jan. 23, 2014, which claims priority to Japanese Patent Application No. 2013-010552, filed Jan. 23, 2013. The International Application was published under PCT Article 21(2) in a language other than English.

TECHNICAL FIELD

The present invention relates to a new organic phosphorus coordination compound catalyst, new phosphine ligand, manufacturing method thereof, as well as use thereof as catalyst in organic synthesis reaction, especially in coupling reaction where aryl, heteroaryl, or vinyl halide or pseudohalide is used as the starting material.

BACKGROUND ART

Coupling reaction is an important reaction in the generation of carbon-carbon bond and carbon-heteroatom bond. Compounds produced by coupling-reaction, such as aromatic amine compounds, are useful as hole-transport materials and luminescent materials used in organic electroluminescence elements, etc., and numerous structures are proposed for these compounds. In addition, aromatic compounds manufactured by utilizing the Suzuki-Miyaura reaction are used as intermediates in numerous drugs, agrochemicals and pigments.

One old method of manufacturing aromatic amine compound is to cause an aromatic compound containing halogen atoms to undergo cross-coupling reaction with a primary amine or secondary amine in the presence of a palladium complex and triaryl phosphine (refer to Patent Literature 1). However, these combinations produce low reactivity and the yield of the target aromatic amine compound is not sufficient, and therefore numerous studies have been conducted, and di-t-butyl (4-dimethyl aminophenyl) phosphine and other catalysts, which have abundant electrons and are sterically bulky, have been proposed as a result (refer to Patent Literature 2). There are also reports on Suzuki-Miyaura reactions using various phosphine ligands (refer to Non-patent Literatures 1 and 2).

BACKGROUND ART LITERATURE

Patent Literature

Patent Literature 1: U.S. Pat. No. 5,576,460
Patent Literature 2: Japanese Patent Laid-open No. 2009-298773

Non-Patent Literature

Non-patent Literature 1: The Journal of Organic Chemistry, 2007, Vol. 72, pp. 5104-5112
Non-patent Literature 2: Chemical Reviews, 1995, Vol. 95, pp. 2457-2483

SUMMARY OF THE INVENTION

Problems to be Solved by the Invention

Numerous compounds having bulky structure are synthesized in recent years as organic electronic materials and pharmaceutical and agrochemical intermediates. Although they are low in price, there is also a need to produce these compounds through reaction from a substrate having low-reactivity chlorine atoms. For example, the cross-coupling described in Patent Literature 2 involves bulky substitution groups and therefore presents the problem of low yield of the target aromatic amine compound when the reactivity of the substrate is low. This is a common problem found in cross-coupling reactions in general. There is also a need for more active catalysts suitable for reaction systems, whose steric characteristics and electronic characteristics can be fine-tuned.

Accordingly, the object of the present invention is to provide a new organic phosphorus ligand and organic phosphorus coordination compound catalyst that can efficiently promote cross-coupling reaction to obtain the target substance at high yield, as well as a method of manufacturing such ligand/catalyst whose steric characteristics and electronic characteristics can be fine-tuned and which can be used to cause cross-coupling reaction at high yield.

Means for Solving the Problems

The inventors of the present invention studied repeatedly in earnest to achieve the aforementioned object and found that use of a ligand that has a structure to allow for fine-tuning of its steric characteristics and electronic characteristics by changing $R^1$, $R^2$, $R^3$, and $R^4$ in General Formula (1) below would promote cross-coupling reaction at high yield. In other words, the present invention is summarized as follows.

(1) Phosphine compound expressed by General Formula (1) below:

$$\tag{1}$$

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group or heterocyclic group. Note that $R^3$ and $R^4$ have no phosphorus atom and that $R^3$ and $R^4$ are not both hydrogen at the same time.)

(2) Phosphine compound according to (1), wherein $R^1$ and $R^2$ are both a t-butyl group in General Formula (1).

(3) Phosphine compound according to (2), expressed by Formula (2) below:

$$\tag{2}$$

(4) Phosphine compound according to (2), expressed by Formula (3) below:

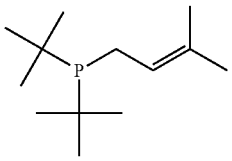

(3)

(5) Coordination compound catalyst constituted by a phosphine compound expressed by General Formula (1) below coordinating to a transition metal selected from the eighth, ninth, tenth, and eleventh families in the periodic table of the elements:

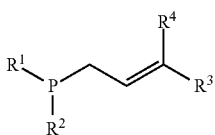

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.)

(6) Coordination compound catalyst according to (5), wherein the transition metal is selected from Pd, Ni, Pt, Rh, Ir, Ru, Co, Fe, Cu, and Au.

(7) Coordination compound according to (6), expressed by Formula (4) below:

$$PdCl_2(tBu_2P-CH_2-CH=CH-CH_3)_2 \quad (4)$$

(In the formula, tBu represents a tertiary butyl group.)

(8) Coordination compound according to (6), expressed by Formula (5) below:

$$PdCl_2(tBu_2P-CH_2-CH=C(CH_3)_2)_2 \quad (5)$$

(In the formula, tBu represents a tertiary butyl group.)

(9) Phosphonium salt compound expressed by General Formula (6) below:

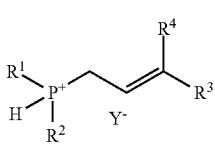

(6)

(In the formula, $R^1$ and $R^2$ are each independently a secondary alkyl group, tertiary alkyl group or cycloalkyl group, while $R^3$ and $R^4$ are each independently a hydrogen, aliphatic group, heteroaliphatic group, aromatic group, alicyclic group, or heterocyclic group, and $Y^-$ represents $B^-F_4$ or $B^-Ph_4$. Note that $R^3$ and $R^4$ have no phosphorus atom and that $R^3$ and $R^4$ are not both hydrogen at the same time.)

(10) Phosphonium salt compound according to (9), wherein $R^1$ and $R^2$ are each a tertiary butyl group in Formula (6).

(11) A method of manufacturing aromatic compound, characterized by using a catalyst or catalyst system which is constituted at least partly by a coordination compound generated by adding to a reaction liquid a phosphine compound expressed by Formula (1) and/or phosphonium salt compound expressed by Formula (6) as well as a transition metal compound selected from the eighth, ninth, tenth, and eleventh families in the periodic table of the elements:

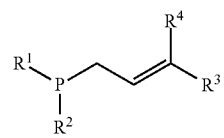

(1)

($R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.)

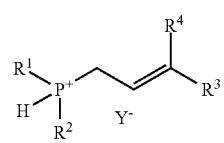

(6)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group, and $Y^-$ represents $B^-F_4$ or $B^-Ph_4$. Note that $R^3$ and $R^4$ have no phosphorus atom and that $R^3$ and $R^4$ are not both hydrogen at the same time.)

(12) A method of manufacturing aromatic compound, characterized by using, as a catalyst or at least as part of a catalyst system, a coordination compound constituted by a phosphine compound expressed by General Formula (1) below coordinating to a transition metal selected from the eighth, ninth, tenth, and eleventh families in the periodic table of the elements:

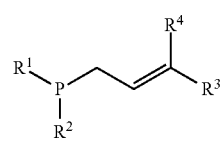

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group or heterocyclic group. Note that $R^3$ and $R^4$ have no phosphorus atom and that $R^3$ and $R^4$ are not both hydrogen at the same time.)

(13) A method of manufacturing aromatic amine compound, which includes: using, as a catalyst or at least as part of a catalyst system, a coordination compound generated by adding to a reaction liquid a phosphine compound expressed by Formula (1) and/or phosphonium salt compound expressed by Formula (6) as well as a transition metal compound selected from the eighth, ninth, tenth, and eleventh families in the periodic table of the elements; and causing an aromatic compound having a halogen atom and/or activated reactive group to react with a primary amine and/or secondary amine:

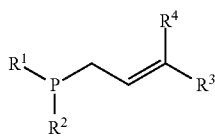

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.)

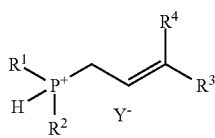

(6)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group, and $Y^-$ represents $B^-F_4$ or $B^-Ph_4$. Note that $R^3$ and $R^4$ have no phosphorus atom and that $R^3$ and $R^4$ are not both hydrogen at the same time.)

(14) A method of manufacturing aromatic amine compound, which includes: using, as a catalyst or at least as part of a catalyst system, a coordination compound constituted by a phosphine compound expressed by General Formula (1) below coordinating to a transition metal selected from the eighth, ninth, tenth, and eleventh families in the periodic table of the elements; and causing an aromatic compound having a halogen atom and/or activated reactive group to react with a primary amine and/or secondary amine:

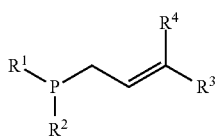

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.)

(15) A method of manufacturing aromatic compound, which includes: using, as a catalyst or at least as part of a catalyst system, a coordination compound generated by adding to a reaction liquid a phosphine compound expressed by Formula (1) and/or phosphonium salt compound expressed by Formula (6) as well as a transition metal compound selected from the eighth, ninth, tenth, and eleventh families in the periodic table of the elements; and causing an aromatic compound having a halogen atom and/or activated reactive group to react with a boron compound:

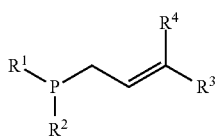

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.)

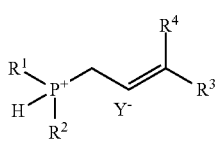

(6)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group, and $Y^-$ represents $B^-F_4$ or $B^-Ph_4$. Note that $R^3$ and $R^4$ have no phosphorus atom and that $R^3$ and $R^4$ are not both hydrogen at the same time.)

(16) A method of manufacturing aromatic compound, which includes: using, as a catalyst or at least as part of a catalyst system, a coordination compound constituted by a phosphine compound expressed by General Formula (1) below coordinating to a transition metal selected from the eighth, ninth, tenth, and eleventh families in the periodic table of the elements; and causing an aromatic compound having a halogen atom and/or activated reactive group to react with a boron compound:

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.)

EFFECTS OF THE INVENTION

Use of the catalyst proposed by the present invention, which has an organic phosphorus compound as a ligand, promotes cross-coupling reaction efficiently. It also allows for fine-tuning of steric characteristics and electronic characteristics as appropriate for the reaction system. As a result, implementing the manufacturing method proposed by the present invention makes it possible to manufacture an aromatic compound at high yield, enabling high-yield production of an aromatic compound such as a biphenyl compound and aromatic amine. In addition, the metal complex proposed by the present invention is stable and easy to handle. Based on the above, the manufacturing method proposed by the present invention is useful in the manufacture of organic electronic materials and pharmaceutical and agrochemical intermediates, thereby offering extremely high value for industrial application.

MODE FOR CARRYING OUT THE INVENTION (Phosphine Compound)

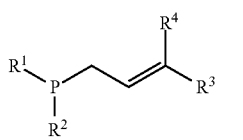

(1)

Under the present invention, $R^1$ and $R^2$ in the phosphine compound expressed by General Formula (1) are each independently a secondary alkyl group, tertiary alkyl group, or cycloalkyl group. In the case of a secondary alkyl group, it is selected from alkyl groups of C3 to C18, or preferably, more advantageously C3 to C6; in the case of a tertiary alkyl group, it is selected from alkyl groups of C4 to C18, or preferably, more advantageously C4 to C8. To be specific, an isopropyl group, s-butyl group, or t-butyl group is preferable. A t-butyl group is the most preferable. In the case of a cycloalkyl group, it may be a monocyclic or polycyclic cycloalkyl group, such as an adamantyl group or norbornyl group. A cycloalkyl group of C3 to C8 is preferable, and a cyclohexyl group is more preferable.

$R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time.

In the case of an aliphatic group, it is an alkyl group of C1 to C18, alkenyl group of C2 to C18, or alkynyl group of C2 to C18, wherein each such group may be either linear or branched. In the case of a heteroaliphatic group, it is an alkyl group, alkenyl group, or alkynyl group containing at least one heteroatom such as an oxygen atom or nitrogen atom, wherein each such group may be either linear or branched. In the case of an alicyclic group, examples include a cycloalkyl group of C3 to C18 and cycloalkenyl group of C5 to C18, wherein each such group may be a monocyclic or polycyclic type. In the case of an aromatic group, examples include monocyclic and polycyclic types. In the case of a heterocyclic group, examples include alicyclic groups having at least one heteroatom in their ring structure and aromatic groups having at least one heteroatom in their ring structure.

The aforementioned substitution group may be substituted further by other substitution groups; for example, an aliphatic group may be substituted by an aromatic group to form an aralkyl group, or the other way around is also possible in that an aromatic group may be substituted by an aliphatic group to form an alkylaryl group.

The most preferable combinations of $R^1$ and $R^2$ include t-butyl group and t-butyl group, cyclohexyl group and cyclohexyl group, and t-butyl group and cyclohexyl group. Combinations of $R^3$ and $R^4$ include methyl group and hydrogen atom, and methyl group and methyl group. To be specific, di-t-butyl crotyl phosphine, di-t-butyl prenyl phosphine, dicyclohexyl crotyl phosphine, dicyclohexyl prenyl phosphine, t-butyl cyclohexyl crotyl phosphine, and t-butyl cyclohexyl prenyl phosphine are applicable.

Di-t-butyl aryl phosphine, di-t-butyl-n-butyl phosphine, and other compounds having a similar structure as the phosphine compound proposed by the present invention result in a clearly lower yield of cross-coupling reaction compared to the phosphine compound proposed by the present invention, as shown in Comparative Examples 2 and 9 described later. On the other hand, the yield of cross-coupling reaction clearly improves when the $R^3$ and $R^4$ combination in the General Formula (1) compound according to the present invention comprises methyl group and hydrogen atom, or when the combination comprises methyl group and methyl group, and this also supports that the effects of the present invention are special and excellent.

In addition, changing the groups constituting $R^1$ and $R^2$ and/or $R^3$ and $R^4$ according to the reaction system allows for fine-tuning of steric characteristics and electronic characteristics. For example, the reaction in Example 10 was effective when di-t-butyl crotyl phosphine was used where the $R^3$ and $R^4$ combination comprised methyl group and hydrogen atom, whereas the reaction in Example 12 was effective when di-t-butyl prenyl phosphine was used where the $R^3$ and $R^4$ combination comprised methyl group and methyl group.

Under the present invention, especially as is evident from the compound of Formula (1), a phosphine compound that enables cross-coupling reaction at higher yield is obtained by changing the electron density of an internal olefin (at least one of $R^3$ and $R^4$ is not a hydrogen atom), not a terminal olefin (i.e., $R^3$ and $R^4$ are both a hydrogen atom).

Examples of such phosphine compound proposed by the present invention include, but are not limited to, the compounds listed below:

Diisopropyl crotyl phosphine, diisopropyl prenyl phosphine, diisopropyl-2-pentenyl phosphine, diisopropyl-5-methyl-2-hexenyl phosphine, diisopropyl-3-cyclohexyl-2-propenyl phosphine, diisopropyl-4-fluoro-2-butenyl phosphine, diisopropyl-4-methoxy-2-butenyl phosphine, diisopropyl-4-dimethyl amino-2-butenyl phosphine, diisopropyl-2,4-hexadienyl phosphine, diisopropyl-2-hexe-4-in-1-yl phosphine, diisopropyl cinnamyl phosphine, diisopropyl-3-(4-fluorophenyl) propenyl phosphine, diisopropyl-3-(4-methoxy phenyl) propenyl phosphine, diisopropyl-3-(4-dimethyl aminophenyl) propenyl phosphine, diisopropyl-3-(2-furyl) propenyl phosphine, diisopropyl-3-(2-pyridyl) propenyl phosphine, diisopropyl-3-(2-thienyl) propenyl phosphine, dicyclohexyl crotyl phosphine, dicyclohexyl prenyl phosphine, dicyclohexyl-2-pentenyl phosphine, dicyclohexyl-5-methyl-2-hexenyl phosphine, dicyclohexyl-3-cyclohexyl-2-propenyl phosphine, dicyclohexyl-4-fluoro-2-butenyl phosphine, dicyclohexyl-4-methoxy-2-butenyl phosphine, dicyclohexyl-4-dimethyl amino-2-butenyl phosphine, dicyclohexyl-2,4-hexadienyl phosphine, dicyclohexyl-2-hexe-4-in-1-yl phosphine, dicyclohexyl cinnamyl phosphine, dicyclohexyl-3-(4-fluorophenyl) propenyl phosphine, dicyclohexyl-3-(4-methoxy phenyl) propenyl phosphine, dicyclohexyl-3-(4-dimethyl aminophenyl) propenyl phosphine, dicyclohexyl-3-(2-furyl) propenyl phosphine, dicyclohexyl-3-(2-pyridyl) propenyl phosphine, dicyclohexyl-3-(2-thienyl) propenyl phosphine, di-t-butyl crotyl phosphine, di-t-butyl prenyl phosphine, di-t-butyl-2-pentenyl phosphine, di-t-butyl-5-methyl-2-hexenyl phosphine, di-t-butyl-3-cyclohexyl-2-propenyl phosphine, di-t-butyl-4-fluoro-2-butenyl phosphine, di-t-butyl-4-methoxy-2-butenyl phosphine, di-t-butyl-4-dimethyl amino-2-butenyl phosphine, di-t-butyl-2,4-hexadienyl phosphine, di-t-butyl-2-hexe-4-in-1-yl phosphine, di-t-butyl cinnamyl phosphine, di-t-butyl-3-(4-fluorophenyl) propenyl phosphine, di-t-butyl-3-(4-methoxy phenyl) propenyl phosphine, di-t-butyl-3-(4-dimethyl aminophenyl) propenyl phosphine, di-t-butyl-3-(2-furyl) propenyl phosphine, di-t-butyl-3-(2-pyridyl) propenyl phosphine, and di-t-butyl-3-(2-thienyl) propenyl phosphine.

(Synthesis of Phosphine Compound)

The phosphine compound proposed by the present invention, expressed by General Formula (1), can be synthesized by causing a Grignard reagent expressed by General Formula (8) to react with a dialkyl phosphinous chloride expressed by General Formula (7) using a copper compound as a catalyst. In General Formula (7), $R^1$ and $R^2$ are each independently a secondary alkyl group of C3 to C18, tertiary alkyl group of C4 to C18, or cycloalkyl group of C3 to C18, or more advantageously secondary alkyl group of C3 to C6, tertiary alkyl group of C4 to C8, or cycloalkyl group of C3 to C8. Specific examples of secondary alkyl group and tertiary alkyl group include preferably isopropyl group, s-butyl group, and t-butyl group. T-butyl group is the most preferable. In the case of a cycloalkyl group, it may be a monocyclic or polycyclic group such as adamantyl group and norbonyl group. A preferable form of cycloalkyl group is cyclohexyl group.

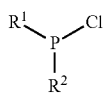 (7)

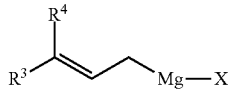 (8)

In a Grignard reagent expressed by General Formula (8), $R^3$ and $R^4$ are each independently a hydrogen, aliphatic group, heteroaliphatic group, aromatic group, alicyclic group, or heterocyclic group. Note that $R^3$ and $R^4$ have no phosphorus atom and that $R^3$ and $R^4$ are not both hydrogen at the same time. In the case of an aliphatic group, it is an alkyl group, alkenyl group, or alkynyl group, wherein each such group may be either linear or branched. In the case of a heteroaliphatic group, it is an alkyl group, alkenyl group, or alkynyl group having an adduct or skeletal group that contains at least one bonded atom being a heteroatom, such as oxygen atom, or nitrogen, wherein each such group may be either linear or branched. In the case of an alicyclic group, examples include cycloalkyl group and cycloalkenyl group of either monocyclic or polycyclic type. In the case of an aromatic group, examples include monocyclic and polycyclic types. In the case of a heterocyclic group, examples include alicyclic groups having at least one heteroatom in their ring structure, and aromatic groups having at least one heteroatom in their ring structure.

The aforementioned substitution group may be substituted further by other substitution groups; for example, an aliphatic group may be substituted by an aromatic group to form an aralkyl group, or the other way around is also possible in that an aromatic group may be substituted by an aliphatic group to form an alkylaryl group.

The most preferable combination of $R^3$ and $R^4$ comprises methyl group and hydrogen atom.

Also, X represents a chlorine atom, bromine atom, or iodine atom.

Similar results can be obtained by using a reaction solvent constituted by ether solvent such as tetrahydrofuran or diethyl ether, alone or mixed with an aromatic solvent such as benzene or toluene, or hydrocarbon solvent such as hexane or heptane.

For example, a di-t-butyl crotyl phosphine expressed by General Formula (2) can be obtained by dripping a Grignard reagent of crotyl chloride or 3-chloro-1-butene into di-t-butyl phosphinous chloride in the presence of a copper catalyst.

An appropriate quantity of copper compound used is 0.1 percent by mol to 10 percent by mol relative to the dialkyl phosphinous halide of General Formula (7). A particularly preferable quantity of copper compound used is 0.5 percent by mol to 3 percent by mol relative to the dialkyl phosphinous halide of General Formula (7). Also regarding the type of this copper compound, either inorganic copper or organic copper can be used, but copper halide or copper (II) acetyl acetonate is particularly preferable.

In addition, the quantity of Grignard reagent of General Formula (8) used in the synthesis method of phosphine compound proposed by the present invention is 0.5 equivalent weight to 5 equivalent weight relative to the dialkyl phosphinous halide of General Formula (7). A preferable quantity of Grignard reagent of General Formula (8) used is 0.9 equivalent weight to 1.5 equivalent weight relative to the dialkyl phosphinous halide of General Formula (7).

The processing method after the end of reaction need only follow any normal synthesis method of tertiary phosphine compound using the Grignard reagent. To be specific, the target tertiary phosphine of General Formula (1) can be obtained by mixing into a reaction system enough water or dilute sulfuric acid or other dilute acid aqueous solution needed to dissolve the inorganic salt, in order to remove inorganic salt byproducts such as magnesium halide, and then separating and removing the water layer, followed by distilling the remaining organic layer at normal pressure or reduced pressure to remove the solvent used.

If isomerization presents a problem, other manufacturing methods may be used, such as causing phosphinous halide to react with organo-lithium reagent, causing dialkyl phosphine to react with olefin, causing dialkyl phosphine to react with alkenyl halide, and causing phosphide prepared from phosphinous halide and metal lithium to react with alkenyl halide. Note, however, that the manufacturing method is not at all limited to the foregoing.

Organic Phosphorus Coordination Compound Catalyst (Constituted by Coordinated Phosphine Compound)

One embodiment of the present invention is a coordination compound constituted by the aforementioned phosphine compound coordinating to a transition metal, particularly a transition metal selected from the eighth, ninth, tenth, and eleventh families in the periodic table of the elements. It is advantageous to select the transition metal from Pd, Ni, Pt, Rh, Ir, Ru, Co, Fe, Cu, and Au, but it is more advantageous to use Pd or Ni for this metal, and most advantageous to use Pd for this metal. Examples of such coordination compound proposed by the present invention include, but are not limited to, the compounds listed below:

Bis (diisopropyl crotyl phosphine) palladium, bis(diisopropyl prenyl phosphine) palladium, bis(bis(diisopropyl-2-pentenyl phosphine) palladium, bis(diisopropyl-5-methyl-2-hexenyl phosphine) palladium, bis(diisopropyl-3-cyclohexyl-2-propenyl phosphine) palladium, bis(diisopropyl-4-fluoro-2-butenyl phosphine) palladium, bis(diisopropyl-4-methoxy-2-butenyl phosphine) palladium, bis(diisopropyl-4-dimethyl amino-2-butenyl-phosphine) palladium, bis(diisopropyl-2,4-hexadienyl phosphine) palladium, bis(diisopropyl-2-hexe-4-in-1-yl phosphine) palladium, bis(diisopropyl cinnamyl phosphine) palladium, bis (diisopropyl-3-(4-fluorophenyl) propenyl phosphine) palladium, bis(diisopropyl-3-(4-methoxy phenyl) propenyl phosphine) palladium, bis (diisopropyl-3-(4-dimethyl aminophenyl) propenyl phosphine) palladium, bis(diisopropyl-3-(2-furyl) propenyl phosphine) palladium, bis(diisopropyl-3-(2-pyridyl) propenyl phosphine) palladium, bis(diisopropyl-3-(2-thienyl) propenyl phosphine) palladium, bis (dicyclohexyl crotyl phosphine) palladium, bis(dicyclohexyl prenyl phosphine) palladium, bis(dicyclohexyl-2-pentenyl phosphine) palladium, bis(dicyclohexyl-5-methyl-2-hexenyl phosphine) palladium, bis(dicyclohexyl-3-cyclohexyl-2-propenyl phosphine) palladium, bis(dicyclohexyl-4-fluoro-2-butenyl phosphine) palladium, bis(dicyclohexyl-4-methoxy-2-butenyl phosphine) palladium, bis(dicyclohexyl-4-dimethyl amino-2-butenyl phosphine) palladium, bis (dicyclohexyl-2,4-hexadienyl phosphine) palladium, bis (dicyclohexyl-2-hexe-4-in-1-yl phosphine) palladium, bis (dicyclohexyl cinnamyl phosphine) palladium, bis (dicyclohexyl-3-(4-fluorophenyl) propenyl phosphine) palladium, bis(dicyclohexyl-3-(4-methoxy phenyl) propenyl phosphine) palladium, bis(dicyclohexyl-3-(4-dimethyl aminophenyl) propenyl phosphine) palladium, bis(dicyclohexyl-3-(2-furyl) propenyl phosphine) palladium, bis(dicyclohexyl-3-(2-pyridyl) propenyl phosphine) palladium, bis (dicyclohexyl-3-(2-thienyl) propenyl phosphine) palladium, bis(di-t-butyl crotyl phosphine) palladium, bis(di-t-butyl prenyl phosphine) palladium, bis(di-t-butyl-2-pentenyl phosphine) palladium, bis(di-t-butyl-5-methyl-2-hexenyl phosphine) palladium, bis(di-t-butyl-3-cyclohexyl-2-propenyl phosphine) palladium, bis(di-t-butyl-4-fluoro-2-butenyl phosphine) palladium, bis(di-t-butyl-4-methoxy-2-butenyl phosphine) palladium, bis(di-t-butyl-4-dimethyl amino-2-butenyl phosphine) palladium, bis(di-t-butyl-2,4-hexadienyl phosphine) palladium, bis(di-t-butyl-2-hexe-4-in-1-yl phosphine) palladium, bis(di-t-butyl cinnamyl phosphine) palladium, bis(di-t-butyl-3-(4-fluorophenyl) propenyl phosphine) palladium, bis(di-t-butyl-3-(4-methoxy phenyl) propenyl phosphine) palladium, bis(di-t-butyl-3-(4-dimethyl aminophenyl) propenyl phosphine) palladium, bis(di-t-butyl-3-(2-furyl) propenyl phosphine) palladium, bis(di-t-butyl-3-(2-pyridyl) propenyl phosphine) palladium, bis(di-t-butyl-3-(2-thienyl) propenyl phosphine) palladium, bis(diisopropyl crotyl phosphine) palladium dichloride, bis(diisopropyl prenyl phosphine) palladium dichloride, bis(bis(diisopropyl-2-pentenyl phosphine) palladium dichloride, bis(diisopropyl-5-methyl-2-hexenyl phosphine) palladium dichloride, bis (diisopropyl-3-cyclohexyl-2-propenyl phosphine) palladium dichloride, bis(diisopropyl-4-fluoro-2-butenyl phosphine) palladium dichloride, bis(diisopropyl-4-methoxy-2-butenyl phosphine) palladium dichloride, bis(diisopropyl-4-dimethyl amino-2-butenyl phosphine) palladium dichloride, bis(diisopropyl-2,4-hexadienyl phosphine) palladium dichloride, bis(diisopropyl-2-hexe-4-in-1-yl phosphine) palladium dichloride, bis(diisopropyl cinnamyl phosphine) palladium dichloride, bis(diisopropyl-3-(4-fluorophenyl) propenyl phosphine) palladium dichloride, bis (diisopropyl-3-(4-methoxy phenyl) propenyl phosphine) palladium dichloride, bis(diisopropyl-3-(4-dimethyl aminophenyl) propenyl phosphine) palladium dichloride, bis(diisopropyl-3-(2-furyl) propenyl phosphine) palladium dichloride, bis(diisopropyl-3-(2-pyridyl) propenyl phosphine) palladium dichloride, bis(diisopropyl-3-(2-thienyl) propenyl phosphine) palladium dichloride, bis(dicyclohexyl crotyl phosphine) palladium dichloride, bis(dicyclohexyl prenyl phosphine) palladium dichloride, bis(dicyclohexyl-2-pentenyl phosphine) palladium dichloride, bis(dicyclohexyl-5-methyl-2-hexenyl phosphine) palladium dichloride, bis(dicyclohexyl-3-cyclohexyl-2-propenyl phosphine) palladium dichloride, bis(dicyclohexyl-4-fluoro-2-butenyl phosphine) palladium dichloride, bis(dicyclohexyl-4-methoxy-2-butenyl phosphine) palladium dichloride, bis(dicyclohexyl-4-dimethyl amino-2-butenyl phosphine) palladium dichloride, bis(dicyclohexyl-2,4-hexadienyl phosphine) palladium dichloride, bis(dicyclohexyl-2-hexe-4-in-1-yl phosphine) palladium dichloride, bis(dicyclohexyl cinnamyl phosphine) palladium dichloride, bis(dicyclohexyl-3-(4-fluorophenyl) propenyl phosphine) palladium dichloride, bis(dicyclohexyl-3-(4-methoxy phenyl) propenyl phosphine) palladium dichloride, bis(dicyclohexyl-3-(4-dimethyl aminophenyl) propenyl phosphine) palladium dichloride, bis(dicyclohexyl-3-(2-furyl) propenyl phosphine) palladium dichloride, bis(dicyclohexyl-3-(2-pyridyl) propenyl phosphine) palladium dichloride, bis(dicyclohexyl-3-(2-thienyl) propenyl phosphine) palladium dichloride, bis(di-t-butyl crotyl phosphine) palladium dichloride, bis(di-t-butyl prenyl phosphine) palladium dichloride, bis (di-t-butyl-2-pentenyl phosphine) palladium dichloride, bis (di-t-butyl-5-methyl-2-hexenyl phosphine) palladium dichloride, bis(di-t-butyl-3-cyclohexyl-2-propenyl phosphine) palladium dichloride, bis(di-t-butyl-4-fluoro-2-butenyl phosphine) palladium dichloride, bis(di-t-butyl-4-methoxy-2-butenyl phosphine) palladium dichloride, bis(di-t-butyl-4-dimethyl amino-2-butenyl phosphine) palladium dichloride, bis(di-t-butyl-2,4-hexadienyl phosphine) palladium dichloride, bis (di-t-butyl-2-hexe-4-in-1-yl phosphine) palladium dichloride, bis(di-t-butyl cinnamyl phosphine) palladium dichloride, bis(di-t-butyl-3-(4-fluorophenyl) propenyl phosphine) palladium dichloride, bis(di-t-butyl-3-(4-methoxy phenyl) propenyl phosphine) palladium dichloride, bis(di-t-butyl-3-(4-dimethyl aminophenyl) propenyl phosphine) palladium dichloride, bis(di-t-butyl-3-(2-furyl) propenyl phosphine) palladium dichloride, bis(di-t-butyl-3-(2-pyridyl) propenyl phosphine) palladium dichloride, bis(di-t-butyl-3-(2-thienyl) propenyl phosphine) palladium dichloride, bis(diisopropyl crotyl phosphine) nickel dichloride, bis(diisopropyl prenyl phosphine) nickel dichloride, bis(bis(diisopropyl-2-pentenyl phosphine) nickel dichloride, bis(diisopropyl-5-methyl-2-hexenyl phosphine) nickel dichloride, bis(diisopropyl-3-cyclohexyl-2-propenyl phosphine) nickel dichloride, bis(diisopropyl-4-fluoro-2-butenyl phosphine) nickel dichloride, bis(diisopropyl-4-methoxy-2-butenyl phosphine) nickel dichloride, bis(diisopropyl-4-dimethyl amino-2-butenyl phosphine) nickel dichloride, bis(diisopropyl-2,4-hexadienyl phosphine) nickel dichloride, bis(diisopropyl-2-hexe-4-in-1-yl phosphine) nickel dichloride, bis(diisopropyl cinnamyl phosphine) nickel dichloride, bis(diisopropyl-3-(4-fluorophenyl) propenyl phosphine) nickel dichloride, bis(diisopropyl-3-(4-methoxy phenyl) propenyl phosphine) nickel dichloride, bis(diisopropyl-3-(4- dimethyl aminophenyl) propenyl phosphine) nickel dichloride, bis(diisopropyl-3-(2-furyl) propenyl phosphine) nickel dichloride, bis(diisopropyl-3-(2-pyridyl) propenyl phosphine) nickel dichloride, bis(diisopropyl-3-(2-thienyl) propenyl phosphine) nickel dichloride, bis(dicyclohexyl crotyl phosphine) nickel dichloride, bis(dicyclohexyl prenyl phosphine) nickel dichloride, bis(dicyclohexyl-2-pentenyl phosphine) nickel dichloride, bis(dicyclohexyl-5-methyl-2-hexenyl phosphine) nickel dichloride, bis(dicyclohexyl-3-cyclohexyl-2-propenyl phosphine) nickel dichloride, bis (dicyclohexyl-4-fluoro-2-butenyl phosphine) nickel dichloride, bis(dicyclohexyl-4-methoxy-2-butenyl phosphine) nickel dichloride, bis(dicyclohexyl-4-dimethyl amino-2-butenyl phosphine) nickel dichloride, bis(dicyclohexyl-2,4-hexadienyl phosphine) nickel dichloride, bis(dicyclohexyl-2-hexe-4-in-1-yl phosphine) nickel dichloride, bis(dicyclohexyl cinnamyl phosphine) nickel dichloride, bis (dicyclohexyl-3-(4-fluorophenyl) propenyl phosphine) nickel dichloride, bis(dicyclohexyl-3-(4-methoxy phenyl) propenyl phosphine) nickel dichloride, bis(dicyclohexyl-3-(4-dimethyl aminophenyl) propenyl phosphine) nickel dichloride, bis (dicyclohexyl-3-(2-furyl) propenyl phosphine) nickel dichloride, bis(dicyclohexyl-3-(2-pyridyl) propenyl phosphine) nickel dichloride, bis(dicyclohexyl-3-(2-thienyl) propenyl phosphine) nickel dichloride, bis(di-t-butyl crotyl phosphine) nickel dichloride, bis(di-t-butyl prenyl phosphine) nickel dichloride, bis(di-t-butyl-2-pentenyl phosphine) nickel dichloride, bis(di-t-butyl-5-methyl-2-hexenyl phosphine) nickel dichloride, bis(di-t-butyl-3-cyclohexyl-2-propenyl phosphine) nickel dichloride, bis(di-t-butyl-4-fluoro-2-butenyl phosphine) nickel dichloride, bis (di-t-butyl-4-methoxy-2-butenyl phosphine) nickel dichloride, bis(di-t-butyl-4-dimethyl amino-2-butenyl phosphine) nickel dichloride, bis(di-t-butyl-2,4-hexadienyl phosphine) nickel dichloride, bis(di-t-butyl-2-hexe-4-in-1-yl phosphine) nickel dichloride, bis(di-t-butyl cinnamyl phosphine) nickel dichloride, bis(di-t-butyl-3-(4-fluorophenyl) propenyl phosphine) nickel dichloride, bis(di-t-butyl-3-(4-methoxy phenyl) propenyl phosphine) nickel dichloride, bis(di-t-butyl-3-(4-dimethyl aminophenyl) propenyl phosphine) nickel dichloride, bis(di-t-butyl-3-(2-furyl) propenyl phosphine) nickel dichloride, bis(di-t-butyl-3-(2-pyridyl) propenyl phosphine) nickel dichloride, and bis(di-t-butyl-3-(2-thienyl) propenyl phosphine) nickel dichloride; among which bis(di-t-butyl crotyl phosphine) palladium, bis(di-t-butyl prenyl phosphine) palladium, bis(di-t-butyl crotyl phosphine) palladium dichloride, bis(di-t-butyl prenyl phosphine) palladium dichloride, bis(di-t-butyl crotyl phosphine) nickel dichloride, and bis(di-t-butyl prenyl phosphine) nickel dichloride are preferable.

The phosphine compound used is normally a distilled or recrystallized product, but it is also possible to use a reaction liquid or its concentrate, or to quaternize a reaction liquid by adding acid and then distill away a top layer and then add alkali and solvent to obtain a top layer and use the obtained top layer. The aforementioned coordination compound can be manufactured beforehand using any known method or other method corresponding thereto, and then used for the catalytic reaction.

Also, as shown in Example 11, a transition metal compound can be used by adding it to the catalytic reaction together with a phosphine compound or phosphonium salt. At this time, the transition metal compound coordinates to the phosphine compound or to the phosphonium salt that has reacted with the alkali in the reaction liquid and become a phosphine compound, so that a reaction similar to the aforementioned catalytic reaction can be promoted.

Examples of nickel compounds indicated as transition metal compounds include nickel (II) chloride, nickel (II) acetate, nickel (II) acetyl acetonate, nickel (II) oxide, bis (cyclooctadiene) nickel (0), and the like. On the other hand, examples of iron compounds include an iron halide such as iron (II) chloride ($FeCl_2$) or iron (III) chloride ($FeCl_3$). Note, however, that these compounds are not limited to the aforementioned examples.

Among the transition metal compounds used, examples of palladium compounds that can be used include palladium (II) acetate, palladium (II) chloride, palladium (II) bromide, sodium tetrachloropalladate (II), palladium (II) acetyl acetonate, palladium (0) dibenzylidene acetone complex, palladium (0) tetrakis (triphenyl phosphine), palladium (0) bis (tri-o-tolyl phosphine), palladium (II) propionate, palladium (II) (cyclooctadiene-1,5) dichloride, palladium (0)-diaryl ether complex, palladium (II) nitrate, palladium (II) chloride bis(acetonitrile), palladium (II) chloride bis(benzonitrile), and other palladium (0) complexes as well as palladium (II) complexes.

When the aforementioned coordination compound is manufactured beforehand, it can be manufactured easily by causing a phosphine compound expressed by General Formula (1) to react with a transition metal or transition metal compound in water, organic solvent, or mixture solvent thereof. For example, a bis(di-t-butyl crotyl phosphine) palladium dichloride expressed by General Formula (4) can be synthesized by adding a methanol solution of sodium tetrachloropalladate (II) to a solution of di-t-butyl crotyl phosphine and then heating the mixture as necessary. Examples of reaction solvents that can be used include water, methanol, ethanol, propanol, and other alcohol solvents, hexane, heptane, and other aliphatic solvents, benzene, toluene, and other aromatic solvents, methylene chloride, chloroform, and other halogen solvents, acetonitrile, benzonitrile, and other nitrile solvents, tetrahydrofuran, diethyl ether, and other ether solvents, and mixture solvents thereof.

(Phosphonium Salt Compound)

The phosphonium salt compound is preferably a phosphonium salt of General Formula (6), especially one whose $R^1$ and $R^2$ are both a tertiary butyl group and $Y^-$ is $B^-F_4$ or $B^-Ph_4$. A phosphonium salt whose $Y^-$ is $B^-F_4$ can be synthesized by adding 40% aqueous solution of fluoroboric acid to a methylene chloride-diluted phosphine compound of General Formula (1) and then condensing the resulting organic layer. Also, the reaction liquid used in the manufacturing process of phosphine compound of General Formula (1) can be used without problem, and if the solubility is low, methylene chloride or other halogen solvent can be used to extract a phosphine compound after adding a 40% aqueous solution of fluoroboric acid and then removing the organic layer. Similarly, a phosphine compound of General Formula (1) can also be synthesized by adding an aqueous solution of sodium tetrafluoroborate to a quaternary salt of such phosphine compound formed by hydrochloric acid, sulfuric acid, or other acid. A phosphonium salt whose $Y^-$ is $B^-Ph_4$ can be synthesized by adding aqueous solution of sodium tetraphenyl borate to a quaternary salt of phosphine compound of General Formula (1) formed by hydrochloric acid, sulfuric acid or other acid.

(How to Use Catalyst)

In general, the quantity of catalyst used is in a range of 0.001 to 50 percent by mol relative to the substrate. This range is preferably 0.01 to 10 percent by mol, or more preferably 0.01 to 5 percent by mol. The mol quantity of phosphine ligand need only be equal to or greater than that of the transition metal, where the ligand can be used at a transition metal/ligand ratio in a range of 1:1 to 1:100. The ratio of transition metal and ligand is preferably 1:1 to 1:10, but a range of 1:1 to 1:5 is particularly preferable. The strict transition metal/ligand ratio to be used depends on the specific application, and also on the quantity of catalyst used. When the transition metal concentration is very low (less than 0.01 percent by mol), therefore, it is generally preferable to use a transition metal/ligand ratio lower than the ratio corresponding to the transition metal concentration of 0.5 to 0.01 percent by mol of transition metal.

Advantageously this catalyst is used in such coupling reaction where C—C bond or C-heteroatom bond is formed. However, it is clear to those skilled in the art that other reactions normally catalyzed by a different transition metal, such as metathesis or double bond or hydrogenation of carbonyl compound, can also be catalyzed by this catalyst.

(Method of Manufacturing Aromatic Amine Compound)

The present invention provides a method of manufacturing aromatic amine compound that includes causing an aromatic compound having a halogen atom and/or activated reactive group to react with a primary amine and/or secondary amine in organic solvent in the presence of a transition metal catalyst and base, as expressed by the reaction formula below:

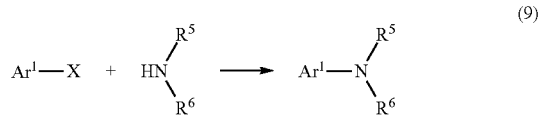

(9)

In the formula, $Ar^1$ represents an aromatic hydrocarbon group that can have a substitution group, or aromatic complex heterocyclic group that can have a substitution group, while X represents an activated reactive group. Examples of X include chlorine atom, bromine atom, iodine atom and sulfonate group, or specifically bromobenzene, 2-bromoanisole, 3-bromoanisole, 4-bromoanisole, 2-bromotoluene, 3-bromotoluene, 4-bromotoluene, 2-bromophenol, 3-bromophenol, 4-bromophenol, 2-bromobenzonitrile, 3-bromobenzonitrile, 4-bromobenzonitrile, 2-bromobenzotrifluoride, 3-bromobenzotrifluoride, 4-bromobenzotrifluoride, 1-bromo-2,4-dimethoxy benzene, 1-bromo-2,5-dimethoxy benzene, 2-bromophenetyl alcohol, 3-bromophenetyl alcohol, 4-bromophenetyl alcohol, 5-bromo-1,2,4-trimethyl benzene, 2-bromo-1,3-dimethyl benzene, 2-bromo-1,4-dimethyl benzene, 3-bromo-1,2-dimethyl benzene, 4-bromo-1,2-dimethyl benzene, 4-bromo-1,3-dimethyl benzene, 5-bromo-1,3-dimethyl benzene, 1-bromo-3-(trifluoromethoxy)benzene, 1-bromo-4-(trifluoromethoxy)benzene, 2-bromobiphenyl, 3-bromobiphenyl, 4-bromobiphenyl, 4-bromo-1,2-(methylene dioxy)benzene, 1-bromonaphthalene, 2-bromonaphthalene, 1-bromo-2-methyl naphthalene, 1-bromo-4-methyl naphthalene, 1-bromo-9H-fluolene, 2-bromo-9H-fluorene, and other aryl bromides; chlorobenzene, 2-chloroanisole, 3-chloroanisole, 4-chloroanisole, 2-chlorotoluene, 3-chlorotoluene, 4-chlorotoluene, 2-chlorophenol, 3-chlorophenol, 4-chlorophenol, 2-chlorobenzonitrile, 3-chlorobenzonitrile, 4-chlorobenzonitrile, 2-chlorobenzotrifluoride, 3-chlorobenzotrifluoride, 4-chlorobenzotrifluoride, 1-chloro-2,4-dimethoxy benzene, 1-chloro-2,5-dimethoxy benzene, 2-chlorophenetyl alcohol, 3-chlorophenetyl alcohol, 4-chlorophenetyl alcohol, 5-chloro-1,2,4-trimethyl benzene, 2-chloro-1,3-dimethyl benzene, 2-chloro-1,4-dimethyl benzene, 3-chloro-1,2-dimethyl benzene, 4-chloro-1,2-dimethyl benzene, 4-chloro-1,3-dimethyl benzene, 5-chloro-1,3-dimethyl benzene, 1-chloro-3-(trifluoromethoxy)benzene, 1-chloro-4-(trifluoromethoxy) benzene, 2-chlorobiphenyl, 3-chlorobiphenyl, 4-chlorobiphenyl, 4-chloro-1,2-(methylene dioxy)benzene, 1-chloro-naphthalene, 2-chloro-naphthalene, 1-chloro-2-methyl naphthalene, 1-chloro-4-methyl naphthalene, 1-chloro-9H-fluorene, 2-chloro-9H-fluorene, and other aryl chlorides; iodobenzene, 2-iodoanisole, 3-iodoanisole, 4-iodoanisole, 2-iodotoluene, 3-iodotoluene, 4-iodotoluene, 2-iodophenol, 3-iodophenol, 4-iodophenol, 2-iodobenzonitrile, 3-iodobenzonitrile, 4-iodobenzonitrile, 2-iodobenzotrifluoride, 3-iodobenzotrifluoride, 4-iodobenzotrifluoride, 1-iodo-2,4-dimethoxy benzene, 1-iodo-2,5-dimethoxy benzene, 2-iodophenetyl alcohol, 3-iodophenetyl alcohol, 4-iodophenetyl alcohol, 5-iodo-1,2,4-trimethyl benzene, 2-iodo-1,3-dimethyl benzene, 2-iodo-1,4-dimethyl benzene, 3-iodo-1,2-dimethyl benzene, 4-iodo-1,2-dimethyl benzene, 4-iodo-1,3-dimethyl benzene, 5-iodo-1,3-dimethhyl benzene, 1-iodo-3-(trifluoromethoxy)benzene, 1-iodo-4-(trifluoromethoxy)benzene, 2-iodobiphenyl, 3-iodobiphenyl, 4-iodobiphenyl, 4-iodo-1,2-(methylene dioxy)benzene, 1-iodo-naphthalene, 2-iodo-naphthalene, 1-iodo-2-methyl naphthalene, 1-iodo-4-methyl naphthalene, and other aryl iodides; fluorobenzene, 2-fluoroanisole, 3-fluoroanisole, 4-fluoroanisole, 2-fluorotoluene, 3-fluorotoluene, 4-fluorotoluene, 2-fluorophenol, 3-fluorophenol, 4-fluorophenol, 2-fluorobenzonitrile, 3-fluorobenzonitrile, 4-fluorobenzonitrile, 2-fluorobenzotrifluoride, 3-fluorobenzotrifluoride, 4-fluorobenzotrifluoride, 1-fluoro-2,4-dimethoxy benzene, 1-fluoro-2,5-dimethoxy benzene, 2-fluorophenetyl alcohol, 3-fluorophenetyl alcohol, 4-fluorophenetyl alcohol, 5-fluoro-1,2,4-trimethyl benzene, 2-fluoro-1,3-dimethyl benzene, 2-fluoro-1,4-dimethyl benzene, 3-fluoro-1,2-dimethyl benzene, 4-fluoro-1,2-dimethyl benzene, 4-fluoro-1,3-dimethyl benzene, 5-fluoro-1,3-dimethyl benzene, 1-fluoro-3-(trifluoromethoxy)benzene, 1-fluoro-4-(trifluoromethoxy) benzene, 2-fluorobiphenyl, 3-fluorobiphenyl, 4-fluorobiphenyl, 4-fluoro-1,2-(methylene dioxy)benzene, 1-fluoro-naphthalene, 2-fluoro-naphthalene, 1-fluoro-2-methyl naphthalene, 1-fluoro-4-methyl naphthalene, and other aryl fluorides; aryl sulfonates such as trifluoromethane sulfonyl oxy benzene, 2-trifluoromethane sulfonyl oxy anisole, 3-trifluoromethane sulfonyl oxy anisole, 4-trifluoromethane sulfonyl oxy anisole, 2-trifluoromethane sulfonyl oxy toluene, 3-trifluoromethane sulfonyl oxy toluene, 4-trifluoromethane sulfonyl oxy toluene, 2-trifluoromethane sulfonyl oxy phenol, 3-trifluoromethane sulfonyl oxy phenol, 4-trifluoromethane sulfonyl oxy phenol, 2-trifluoromethane sulfonyl oxy benzonitrile, 3-trifluoromethane sulfonyl oxy benzonitrile, 4-trifluoromethane sulfonyl oxy benzonitrile, 2-trifluoromethane sulfonyl oxy benzotrifluoride, 3-trifluoromethane sulfonyl oxy benzotrifluoride, 4-trifluoromethane sulfonyl oxy benzotrifluoride, 1-trifluoromethane sulfonyl oxy-2,4-dimethoxy benzene, 1-trifluoromethane sulfonyl oxy-2,5-dimethoxy benzene, 2-trifluoromethane sulfonyl oxy phenetyl alcohol, 3-trifluoromethane sulfonyl oxy phenetyl alcohol, 4-trifluoromethane sulfonyl oxy phenetyl alcohol, 5-trifluoromethane sulfonyl oxy-1,2,4-trimethyl benzene, 2-trifluoromethane sulfonyl oxy-1,3-dimethyl benzene, 2-trifluoromethane sulfonyl oxy-1,4-dimethyl benzene, 3-trifluoromethane sulfonyl oxy-1,2-dimethyl benzene, 4-trifluoromethane sulfonyl oxy-1,2-dimethyl benzene, 4-trifluoromethane sulfonyl oxy-1,3-dimethyl benzene, 5-trifluoromethane sulfonyl oxy-1,3-dimethyl benzene, 1-trifluoromethane sulfonyl oxy-3-(trifluoromethoxy) benzene, 1-trifluoromethane sulfonyl oxy-4-

(trifluoromethoxy)benzene, 2-trifluoromethane sulfonyl oxy biphenyl, 3-trifluoromethane sulfonyl oxy biphenyl, 4-trifluoromethane sulfonyl oxy biphenyl, 4-trifluoromethane sulfonyl oxy-1,2-(methylene dioxy)benzene, 1-trifluoromethane sulfonyl oxy naphthalene, 2-trifluoromethane sulfonyl oxy naphthalene, 1-trifluoromethane sulfonyl oxy-2-methyl naphthalene, 1-trifluoromethane sulfonyl oxy-4-methyl naphthalene, and other aryl trifluoromethane sulfonates; methane sulfonyl oxy benzene, 2-methane sulfonyl oxy anisole, 3-methane sulfonyl oxy anisole, 4-methane sulfonyl oxy anisole, 2-methane sulfonyl oxy toluene, 3-methane sulfonyl oxy toluene, 4-methane sulfonyl oxy toluene, 2-methane sulfonyl oxy phenol, 3-methane sulfonyl oxy phenol, 4-methane sulfonyl oxy phenol, 2-methane sulfonyl oxy benzonitrile, 3-methane sulfonyl oxy benzonitrile, 4-methane sulfonyl oxy benzonitrile, 2-methane sulfonyl oxy benzotrifluoride, 3-methane sulfonyl oxy benzotrifluoride, 4-methane sulfonyl oxy benzotrifluoride, 1-methane sulfonyl oxy-2,4-dimethoxy benzene, 1-methane sulfonyl oxy-2,5-dimethoxy benzene, 2-methane sulfonyl oxy phenetyl alcohol, 3-methane sulfonyl oxy phenetyl alcohol, 4-methane sulfonyl oxy phenetyl alcohol, 5-methane sulfonyl oxy-1,2,4-trimethyl benzene, 2-methane sulfonyl oxy-1,3-dimethyl benzene, 2-methane sulfonyl oxy-1,4-dimethyl benzene, 3-methane sulfonyl oxy-1,2-dimethyl benzene, 4-methane sulfonyl oxy-1,2-dimethyl benzene, 4-methane sulfonyl oxy-1,3-dimethyl benzene, 5-methane sulfonyl oxy-1,3-dimethyl benzene, 1-methane sulfonyl oxy-3-(trifluoromethoxy)benzene, 1-methane sulfonyl oxy-4-(trifluoromethoxy)benzene, 2-methane sulfonyl oxy biphenyl, 3-methane sulfonyl oxy biphenyl, 4-methane sulfonyl oxy biphenyl, 4-methane sulfonyl oxy-1,2-(methylene dioxy)benzene, 1-methane sulfonyl oxy naphthalene, 2-methane sulfonyl oxy naphthalene, 1-methane sulfonyl oxy-2-methyl naphthalene, 1-methane sulfonyl oxy-4-methyl naphthalene, and other aryl methane sulfonates; p-toluene sulfonyl oxy benzene, 2-(p-toluene sulfonyl oxy) anisole, 3-(p-toluene sulfonyl oxy) anisole, 4-(p-toluene sulfonyl oxy) anisole, 2-(p-toluene sulfonyl oxy) toluene, 3-(p-toluene sulfonyl oxy) toluene, 4-(p-toluene sulfonyl oxy) toluene, 2-(p-toluene sulfonyl oxy) phenol, 3-(p-toluene sulfonyl oxy) phenol, 4-(p-toluene sulfonyl oxy) phenol, 2-(p-toluene sulfonyl oxy)benzonitrile, 3-(p-toluene sulfonyl oxy)benzonitrile, 4-(p-toluene sulfonyl oxy)benzonitrile, 2-(p-toluene sulfonyl oxy)benzotrifluoride, 3-(p-toluene sulfonyl oxy)benzotrifluoride, 4-(p-toluene sulfonyl oxy)benzotrifluoride, 1-(p-toluene sulfonyl oxy)-2,4-dimethoxy benzene, 1-(p-toluene sulfonyl oxy)-2,5-dimethoxy benzene, 2-(p-toluene sulfonyl oxy) phenetyl alcohol, 3-(p-toluene sulfonyl oxy) phenetyl alcohol, 4-(p-toluene sulfonyl oxy) phenetyl alcohol, 5-(p-toluene sulfonyl oxy)-1,2,4-trimethyl benzene, 2-(p-toluene sulfonyl oxy)-1,3-dimethyl benzene, 2-(p-toluene sulfonyl oxy)-1,4-dimethyl benzene, 3-(p-toluene sulfonyl oxy)-1,2-dimethyl benzene, 4-(p-toluene sulfonyl oxy)-1,2-dimethyl benzene, 4-(p-toluene sulfonyl oxy)-1,3-dimethyl benzene, 5-(p-toluene sulfonyl oxy)-1,3-dimethyl benzene, 1-(p-toluene sulfonyl oxy)-3-(trifluoromethoxy)benzene, 1-(p-toluene sulfonyl oxy)-4-(trifluoromethoxy)benzene, 2-(p-toluene sulfonyl oxy) biphenyl, 3-(p-toluene sulfonyl oxy) biphenyl, 4-(p-toluene sulfonyl oxy) biphenyl, 4-(p-toluene sulfonyl oxy)-1,2-(methylene dioxy)benzene, 1-(p-toluene sulfonyl oxy) naphthalene, 2-(p-toluene sulfonyl oxy) naphthalene, 1-(p-toluene sulfonyl oxy)-2-methyl naphthalene, 1-(p-toluene sulfonyl oxy)-4-methyl naphthalene, and other aryl p-toluene sulfonates; and the like. In addition, 1,2-dibromobenzene, 1,3-dibromobenzene, 1,4-dibromobenzene, 9,10-dibromoanthracene, 9,10-dichloroanthracene, 4,4'-dibromobiphenyl, 4,4'-dichlorobiphenyl, 4,4'-iodobiphenyl, 1-bromo-2-fluorobenzene, 1-bromo-3-fluorobenzene, 1-bromo-4-fluorobenzene, 1-bromo-2-chlorobenzene, 1-bromo-3-chlorobenzene, 1-bromo-4-chlorobenzene, 2-bromo-5-chlorotoluene, 3-bromo-4-chlorobenzotrifluoride, 5-bromo-2-chlorobenzotrifluoride, 1-bromo-2,3-dichlorobenzene, 1-bromo-2,6-dichlorobenze, 1-bromo-3,5-dichlorobenzene, 2-bromo-4-fluorotoluene, 2-bromo-5-fluorotoluene, 3-bromo-4-fluorotoluene, 4-bromo-2-fluorotoluene, 4-bromo-3-fluorotoluene, 2,7-dibromo-9H-fluolene, 1,8-dibromo-9H-fluolene, 2,7-dichloro-9H-fluolene, 1,8-dichloro-9H-fluorene, 2-bromo-9,9-dimethyl fluolene, 2,7-dibromo-9,9-dimethyl fluolene, and other aryl halides having two or more halogen atoms; 1-chloro-2-trifluoromethane sulfonyl oxy benzene, 1-chloro-3-trifluoromethane sulfonyl oxy benzene, 1-chloro-4-trifluoromethane sulfonyl oxy benzene, 9-chloro-10-trifluoromethane sulfonyl oxy anthracene, 9-chloro-10-trifluoromethane sulfonyl oxy anthracene, 4-chloro-4'-trifluoromethane sulfonyl oxy biphenyl, 4-iodo-4'-trifluoromethane sulfonyl oxy biphenyl, 1-bromo-2-methane sulfonyl oxy benzene, 1-bromo-3-methane sulfonyl oxy benzene, 1-bromo-4-methane sulfonyl oxy benzene, 9-bromo-10-methane sulfonyl oxy anthracene, 9-chloro-10-methane sulfonyl oxy anthracene, 4-bromo-4'-methane sulfonyl oxy biphenyl, 4-chloro-4'-methane sulfonyl oxy biphenyl, 4-iodo-4'-methane sulfonyl oxy biphenyl, 1-bromo-2-(p-toluene sulfonyl oxy)benzene, 1-bromo-3-(p-toluene sulfonyl oxy)benzene, 1-bromo-4-(p-toluene sulfonyl oxy)benzene, 9-bromo-10-(p-toluene sulfonyl oxy) anthracene, 9-chloro-10-(p-toluene sulfonyl oxy) anthracene, 4-bromo-4'-(p-toluene sulfonyl oxy) biphenyl, 4-chloro-4'-(p-toluene sulfonyl oxy) biphenyl, 4-iodo-4'-(p-toluene sulfonyl oxy) biphenyl, and other aryl halides having one or more halogen atoms and one or more sulfonate groups, are also given as examples of aryl halides that can be used in the present invention. Note, however, that the present invention is not limited at all to the foregoing. $R^5$ and $R^6$ may each independently represent a hydrogen (however, $R^5$ and $R^6$ are not both hydrogen at the same time), linear or branched aliphatic hydrocarbon group that can have a substitution group, monocyclic or polycyclic aliphatic hydrocarbon group that can have a substitution group, monocyclic or polycyclic aromatic hydrocarbon group that can have a substitution group, or monocyclic or polycyclic aromatic heterocyclic group that can have a substitution group, or $R^5$ and $R^6$ may form the same ring structure, with the nitrogen atom in the ring being carbazole, piperidine, morpholine, or other condensed heterocyclic ring formed by condensed $R^5$, $R^6$, and nitrogen atom and involved in the reaction. Examples of amines that can be used in the present invention include, but are not limited to, ethyl amine, propyl amine, isopropyl amine, butyl amine, isobutyl amine, s-butyl amine, t-butyl amine, pentyl amine, isopentyl amine, neopentyl amine, hexyl amine, 2-ethyl hexyl amine, cyclopropyl amine, cyclopentyl amine, cyclohexyl amine, heptyl amine, octyl amine, adamantyl amine, benzyl amine, α-methyl benzyl amine, α,α-dimethyl benzyl amine, 2-phenyl ethyl amine, 2-methoxy ethyl amine, 2-ethoxy ethyl amine, 2-methoxy propyl amine, 3-methoxy propyl amine, and other aliphatic primary amines that can have a substitution group; aniline, 2-chloroaniline, 3-chloroaniline, 4-chloroaniline, 2-bromoaniline, 3-bromoaniline, 4-bromoaniline, 2-fluoroaniline, 3-fluoroaniline, 4-fluoroaniline, 2-anisidine, 3-anisidine, 4-anisidine, 2-toluidine, 3-toluidine, 4-toluidine, 2,3-dimethyl aniline, 2,4-dimethyl aniline, 2,6-dimethyl aniline, 3,5-dimethyl aniline, 2,4,6- trimethyl aniline, 2,3-dichloroaniline, 2,4-dichloroaniline, 2,5-dichloroaniline, 2,6-dichloroaniline, 3,5-dichloroaniline, 2,3-difluoroaniline, 2,4-difluoroaniline, 2,6-difluoroaniline, 2-chloro-3-fluoroaniline, 2-chloro-4-fluoroaniline, 2-chloro-5-fluoroaniline, 2-chloro-6-fluoroaniline, 3-chloro-2-fluoroaniline, 3-chloro-4-fluoroaniline, 4-chloro-2-fluoroaniline, 5-chloro-2-fluoroaniline, 6-chloro-2-fluoroaniline, 1-naphtyl amine, 2-naphtyl amine, 2-aminobiphenyl, 4-aminobiphenyl, 1,4-diaminobenzene, 4-dimethyl aminoaniline, 4,4'-diaminobiphenyl, and other aromatic primary amines that can have a substitution group; 2-aminopyridine, 3-aminopyridine, 4-aminopyridine, 2-aminopyrimidine, 4-aminopyrimidine, 3-aminopyrazole, 5-aminopyrazole, 3-aminotriazole, 5-aminotriazole, 2-aminoindole, 3-aminoindole, 2-aminoquinoline, 3-aminoquinoline, 4-aminoquinoline, 7-aminoquinoline, 8-aminoquinoline, 9-aminoanthracene, and other complex aromatic primary amines that can have a substitution group; dimethyl amine, diethyl amine, diisopropyl amine, diisobutyl amine, di-t-butyl amine, dicyclopentyl amine, dicyclohexyl amine, methyl isopropyl amine, ethyl isopropyl amine, methyl-t-butyl amine, methyl cyclohexyl amine, N-methyl benzyl amine, N,α-dimethyl benzyl amine, N, α,α-trimethyl benzyl amine, bis-(2-ethyl hexyl)amine, N-methyl phenetyl amine, and other aliphatic secondary amines that can have a substitution group; piperazine, 2-methyl piperazine, homopiperazine, N-methyl homopiperazine, 2,6-dimethyl piperazine, N-methyl piperazine, N-ethyl piperazine, N-ethoxy carbonyl piperazine, N-benzyl piperazine, morpholine, 3,5-dimethyl morpholine, piperidine, 2,6-dimethyl piperidine, 2,2-dimethyl piperidine, 3,5-dimethyl piperidine, 2-ethyl piperidine, 4-piperidone ethylene ketal, pyrrolidine, 2,5-dimethyl pyrrolidine, and other heterocyclic aliphatic amines that can have a substitution group; pyrrole, indole, pyrazole, imidazole, 1,2,4-triazole, carbazole, and other heterocyclic aromatic amines that can have a substitution group; and N-methyl aniline, N-ethyl aniline, N-isopropyl aniline, N-t-butyl aniline, N-methyl-1-naphtyl amine, N-methyl-2-naphtyl amine, 2-methyl aminopyridine, 3-methyl aminopyridine 2-methyl aminopyrimidine, N,N'-diphenyl phenylene diamine, N,N-diphenyl amine, and other aromatic secondary amines that can have a substitution group in the aromatic ring.

Under the manufacturing method proposed by the present invention, preferably the reaction is caused in the presence of (in coexistence with) base. This base can be, for example, sodium carbonate, potassium carbonate, cesium carbonate, sodium hydroxide, potassium hydroxide, potassium phosphate, or other inorganic base; butyl lithium, phenyl lithium, methyl magnesium chloride, phenyl magnesium chloride, or other organic metal base; sodium hexamethyl disilazide, lithium hexamethyl disilazide, or other metal amide; and sodium-t-butoxide, potassium-t-butoxide, sodium methoxide, potassium methoxide, sodium ethoxide, potassium ethoxide, sodium (2,4,6-tri-t-butyl phenolate), potassium (2,4,6-tri-t-butyl phenolate), or other metal alkoxide. Preferably it is metal alkoxide, and more preferably it is sodium-t-butoxide, potassium-t-butoxide, or other alkali metal alkoxide with an alkoxy group of C1 to C6.

Under the manufacturing method proposed by the present invention, preferably the reaction is caused in the presence of organic solvent. Organic solvents that can be used include toluene, xylene (o-xylene, m-xylene, p-xylene and mixtures thereof), mesitylene, p-cymene, ethyl benzene, chlorobenzene, nitrobenzene and other aromatic hydrocarbon solvents; tetrahydrofuran, 1,4-dioxane, and other ether solvents; and mixed solvents thereof; among which toluene, xylene, mesitylene, ethyl benzene, chlorobenzene, and nitrobenzene are preferred, while toluene, xylene, and mesitylene are more preferred, and xylene is most preferred.

(Method of Manufacturing Aromatic Compound)

The present invention provides a method of manufacturing aromatic compound that includes causing an aromatic compound having a halogen atom and/or activated reactive group to react with any organic boron compounds in solvent in the presence of transition metal catalyst and base, as expressed by the reaction formula below:

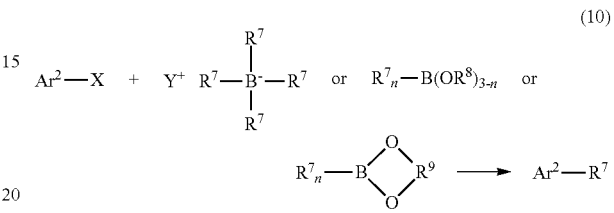

In the formula, $Ar^2$ represents an aromatic hydrocarbon that can have a substitution group, or aromatic heterocyclic compound that can have a substitution group. Also, X represents an activated reactive group, such as chlorine atom, bromine atom, iodine atom, or sulfonate group, whose examples are the same as those presented for $Ar^1$.

In the formula, $R^7$ represents alkyl, alkenyl, alkynyl, or other aliphatic hydrocarbon group that can have a substitution group, aromatic hydrocarbon group that can have a substitution group, or aromatic heterocyclic group that can have a substitution group, while Y represents sodium, potassium, or other counter-cation. Also, $R^8$ represents a hydrogen atom or alkyl group that can have a substitution group, where n is an integer of 1 to 3. Also, $R^9$ represents an allylene group that can have a substitution group, or heterocyclic group that can have a substitution group, or alkylene group that can have a substitution group, with a ring containing —OBO— formed using any of the foregoing as a coupling means for —OBO—. Examples of boronic acids that can be used in the present invention include, but are not limited to, methyl boronic acid, ethyl boronic acid, cyclopropyl boronic acid, butyl boronic acid, cyclohexyl boronic acid, and other alkyl boronic acids; vinyl boronic acid, 1-propene-1-yl boronic acid, 1-propene-2-yl boronic acid, 1-butene-1-yl boronic acid, 1-butene-2-yl boronic acid, 2-butene-2-yl boronic acid, 1-pentene-1-ylboronic acid, α-styryl boronic acid, β-styryl boronic acid, 1,2-diphenyl ethenyl boronic acid, 2,2-diphenyl ethenyl boronic acid, cyclopentenyl boronic acid, cyclohexenyl boronic acid, 2-methyl cyclohexenyl boronic acid, and other alkenyl boronic acids; ethynyl boronic acid, 3-methoxy-1-propine-1-yl boronic acid, cyclopropyl ethynyl boronic acid, 1-pentynyl boronic acid, 3,3-dimethyl-1-butyne-1-yl boronic acid, 2-phenyl-1-ethynyl boronic acid, 5-chloro-1-pentynyl boronic acid, 2-(di-t-butyl dimethyl silanyl)-ethynyl boronic acid, and other alkynyl boronic acids; aryl boronic acids such as phenyl boronic acid, as well as 2-methyl phenyl boronic acid, 3-methyl phenyl boronic acid, 4-methyl phenyl boronic acid, 4-trifluoromethyl phenyl boronic acid, and other alkyl aryl boronic acids; 2-thienyl boronic acid, 2-furyl boronic acid, 2-pyridyl boronic acid, and other boronic acids having a heterocyclic group; 2,3,4,5,6-pentafluorophenyl boronic acid, 2-fluorophenyl boronic acid, 3-fluorophenyl boronic acid, 4-fluorophenyl boronic acid, 2-chlorophenyl boronic acid, 3-chlorophenyl boronic acid, 4-chlorophenyl boronic acid, 2-bromophenyl boronic acid, 3-bromophenyl boronic acid, 4-bromophenyl boronic acid, 2-iodophenyl boronic acid, 3-iodophenyl boronic acid, 4-iodophenyl boronic acid, 2,4-difluorophenyl boronic acid, 3,4-difluorophenyl boronic acid, 2,3-difluorophenyl boronic acid, 3,4,5-trifluorophenyl boronic acid, 2,3,4-trifluorophenyl boronic acid, 2,4,6-trifluorophenyl boronic acid, and other aryl boronic acids having a halogen atom; 2-cyanophenyl boronic acid, 3-cyanophenyl boronic acid, 4-cyanophenyl boronic acid, and other aryl boronic acids having a cyano group; 4-methoxy phenyl boronic acid, 4-t-butoxy phenyl boronic acid, and other alkosialyl boronic acids; 1-naphtyl boronic acid, 9-phenanthrene boronic acid, 9-anthracene boronic acid, ferrocenyl boronic acid, and other polycyclic aryl boronic acids; 2-hydroxy phenyl boronic acid, 3-hydroxy phenyl boronic acid, 4-hydroxy phenyl boronic acid, and other hydroxy aryl boronic acids; and 4-acetyl phenyl boronic acid, 4-formyl phenyl boronic acid, and other aryl boronic acids having a carbonyl substitution group. Esters of these boronic acids (such as dimethyl ester, diethyl ester, dipropyl ester, and pinacol ester), etc., are also cited as examples.

Under the manufacturing method proposed by the present invention, preferably the reaction is caused in the presence of (in coexistence with) base. Any general inorganic base or organic base can be used for the reaction, but preferable examples include sodium hydroxide, potassium hydroxide, and other hydroxides; sodium carbonate ($Na_2CO_3$), potassium carbonate ($K_2CO_3$), cesium carbonate ($Cs_2CO_3$), and other carbonates; sodium acetate, potassium acetate, and other acetates; sodium phosphate ($Na_3PO_4$), potassium phosphate ($K_3PO_4$), and other phosphates; triethyl amines, pyridine, morpholine, quinoline, piperidine, DBU (diaza bicyclo undecene), anilines, tetra n-butyl ammonium acetate, and other ammonium salts, and other organic salts. These bases may be used alone, or two or more of them may be used together.

The manufacturing method proposed by the present invention normally uses solvent, and preferably is implemented in organic solvent. Other solvent, such as water, can also be used. Examples of organic solvents include methanol, ethanol, and other alcohol solvents; N-methyl pyrrolidone, N,N-dimethyl formamide, N,N-dimethyl acetamide, dimethyl sulfoxide, acetonitrile, and other aprotic polar solvents; diethyl ether, diisopropyl ether, ethylene glycol dimethyl ether, diethylene glycol dimethyl ether, 1,4-dioxane, tetrahydrofuran, and other ether solvents; benzene, toluene, xylene, and other aromatic hydrocarbon solvents; and hexane, heptane, and other aliphatic hydrocarbon solvents.

(Other Reactions)

The aforementioned examples of coupling reaction do not limit the types of coupling reaction where the catalyst proposed by the present invention can be used, and it is clear to those skilled in the art that the catalyst proposed by the present invention can be used in the similar coupling reactions listed below.

(a) Stille cross-coupling of organic tin compound with carbon electrophile having halogen or pseudo-halogen as a leaving group;
(b) Hiyama cross-coupling of organosilane with aryl, heteroaryl, or vinyl halide or pseudo-halide;
(c) Negishi cross-coupling of organic zinc compound with aryl, heteroaryl, or vinyl halide or pseudo-halide;
(d) Kumada cross-coupling of Grignard compound with aryl, heteroaryl, or vinyl halide or pseudo-halide;
(e) Sonogashira cross-coupling of terminal alkyne with aryl, heteroaryl, or vinyl halide or pseudo-halide;
(f) α-arylation of enolate or other stabilized carbanion by aryl or heteroaryl halide or pseudo-halide;
(g) Cyanidation of aryl or heteroaryl halide or pseudo-halide;
(h) Carbonylation of aryl or heteroaryl halide or pseudo-halide; and
(i) Heck coupling of aryl, heteroaryl, or vinyl halide or pseudo-halide to olefin.

EXAMPLES

All chemicals were purchased from their distributors/suppliers as reagents, and unless otherwise indicated, used without further refinement. For tetrahydrofuran (THF), dehydrated solvent was used. All proton (1H) NMR (nuclear magnetic resonance spectrum) data was recorded at 400 MHz using the JNM-ESC400 (manufactured by JEOL Ltd.). Chemical shifts are indicated in parts per million (ppm) on the delta scale (δ), and tetramethyl silane (δ=0 ppm) is referenced in the interpretation of 1H NMR.

The present invention is explained in greater detail below, but it should be noted that the present invention is not at all limited to these examples.

In the examples below, purities (%) are area percentages obtained by gas chromatography analysis. Also, additive quantities of copper compounds are accompanied by a percent-by-mol value relative to dialkyl phosphinous chloride.

Example 1

Manufacture of Di-t-Butyl Crotyl Phosphine 70 ml of tetrahydrofuran, 140 ml of toluene, 53.1 g (0.28 mol) of di-t-butyl phosphinous chloride, and 0.83 g (0.0084 mol (corresponding to 3 percent by mol)) of copper (I) chloride were introduced to a fully nitrogen-replaced four-neck flask of 1 L in capacity. Into this flask, a Grignard reagent solution prepared in advance from 27.9 g (0.31 mol) of crotyl chloride and 15.0 g (0.62 mol) of metal magnesium in 327 ml of tetrahydrofuran was dripped over 2 hours by maintaining temperatures between 10° C. and 20° C. When the dripping was completed, the mixture was agitated for 3 hours at temperatures between 10° C. and 20° C. The reaction liquid was returned to 25° C., and then loss of di-t-butyl phosphinous chloride was checked by gas chromatography. Thereafter, 62 ml of 3% aqueous solution of sulfuric acid was added to the reaction liquid to separate the organic layer, which was then washed in water and dried with anhydrous sodium sulfate. Furthermore, the solvent was distilled away under reduced pressure and then distilled to collect the fraction of distillate at 80° C. under a reduced pressure of 1.1 torr (146.63 Pa), to obtain 31.0 g (purity 97.0%) of target di-t-butyl crotyl phosphine as a viscous, oily substance. The yield was 54%.

Mass spectrum (EI method) M/Z 200 (M+)

1H-NMR spectrum ($CDCl_3$) δ ppm: 1.14, 1.15 (d, J=11.0 Hz, 18H, (C$\underline{H}_3$C)$_2$—P— (cis isomer+trans isomer)), 1.62-1.73 (m, 3H, —CH=CH—C$\underline{H}_3$(cis isomer+trans isomer)), 2.4 (br-s, 2H, (CH$_3$C)$_2$P—C $\underline{H}_2$— (cis isomer+trans isomer)), 5.39-5.74 (m, 2H, —C$\underline{H}$=C$\underline{H}$—CH$_3$ (cis isomer+trans isomer)).

Example 2

Manufacture of Bis(Di-t-Butyl Crotyl Phosphine) Palladium Dichloride 11 ml of hexane and 7.2 g (0.036 mol) of di-t-butyl crotyl phosphine were introduced to a fully nitrogen-replaced four-neck flask of 200 ml in capacity. Into this flask, 66.4 g (0.018 mol) of methanol solution of sodium tetrachloropalladate (II) was introduced and the mixture was heated to reflux for 10 minutes. Next, the mixture was cooled to 25° C., and then filtered and washed with 27 ml of methanol. The obtained solids were dried to obtain 9.8 g of target bis(di-t-butyl crotyl phosphine) palladium dichloride as yellow solids. The yield was 94%.

1H-NMR spectrum (CDCl$_3$) δ ppm: 1.49-1.53 (18H, (CH$_3$C)$_2$—P— (cis isomer+trans isomer)), 1.65-1.73 (m, 3H, —CH=CH—CH$_3$(cis isomer+trans isomer)), 2.88 (br-s, 2H, (CH$_3$C)$_2$P—CH$_2$— (cis isomer+trans isomer)), 5.54-5.55 (m, 1H, —CH=CH—CH$_3$(cis isomer+trans isomer)), 5.86-5.87 (m, 1H, —CH=CH—CH$_3$ (cis isomer+trans isomer))

Melting point: 180° C. (Breakdown occurred)

Example 3

Manufacture of Di-t-Butyl Crotyl Phosphonium Tetrafluoroborate 15 ml of hexane and 4.0 g (0.020 mol) of di-t-butyl crotyl phosphine were introduced to a fully nitrogen-replaced four-neck flask of 300 ml in capacity. Into this flask, 4.38 g (0.021 mol) of 40% aqueous solution of fluoroboric acid was introduced and the mixture was agitated at 25° C. Thereafter, 30 ml of toluene was introduced to the obtained bottom layer and the mixture was agitated at 25° C. and separated. Next, 30 ml of methylene chloride was introduced to the obtained bottom layer and the mixture was agitated at 25° C. The solvent was distilled away from the obtained organic layer under reduced pressure, to obtain 5.4 g of target di-t-butyl crotyl phosphonium tetrafluoroborate as white solids. The yield was 95%.

1H-NMR spectrum (D$_2$O) δ ppm: 1.38, 1.40 (d, J=16.7 Hz, 18H, (CH$_3$C)$_2$—P— (cis isomer+trans isomer)), 1.59-1.64 (m, 3H, —CH=CH—CH$_3$(cis isomer+trans isomer), 3.10, 3.13 (dd, J=12.5 Hz, 7.4 Hz, 2H, (CH$_3$C)$_2$P—CH$_2$— (cis isomer+trans isomer)), 5.42-5.48 (m, 1H, —CH=CH—CH$_3$ (cis isomer+trans isomer)), 5.77-5.84 (m, 1H, —CH=CH—CH$_3$ (cis isomer+trans isomer))

Melting point: 110° C.

Example 4

Manufacture of Di-t-Butyl Crotyl Phosphonium Tetraphenyl Borate 2.7 ml of tetrahydrofuran, 5.5 ml of toluene, 7.1 g (0.039 mol) of di-t-butyl phosphinous chloride, and 0.12 g (0.0012 mol (corresponding to 3 percent by mol)) of copper (I) chloride were introduced to a fully nitrogen-replaced four-neck flask of 100 ml in capacity. Into this flask, a Grignard reagent solution prepared in advance from 3.9 g (0.043 mol) of crotyl chloride and 2.1 g (0.086 mol) of metal magnesium in 41 ml of tetrahydrofuran was dripped over 20 minutes by maintaining temperatures between 30° C. and 45° C. When the dripping was completed, the mixture was agitated for 3 hours at temperatures between 30° C. and 40° C. The reaction liquid was returned to 25° C., and then loss of di-t-butyl phosphinous chloride was checked by gas chromatography. Thereafter, 13 ml of 3% aqueous solution of sulfuric acid was added to the reaction liquid to separate the organic layer, which was then washed in water. Next, 54 ml of 10% aqueous solution of sulfuric acid was added and the mixture was agitated for 30 minutes and then separated. The bottom layer was washed with 10 ml of toluene, after which 15 ml of hexane and 20 ml of 20% aqueous solution of sodium hydroxide were added and the mixture was agitated for 30 minutes and separated. The top layer was washed in water, 10.4 g (0.021 mol) of 20% aqueous solution of sulfuric acid was introduced, and the mixture was agitated at 25° C. Next, 4.0 g (0.020 mol) of 20% aqueous solution of sodium hydroxide was introduced and the mixture was agitated at 25° C. Furthermore, 11.5 g (0.021 mol) of 18.7% aqueous solution of sodium tetraphenyl borate was introduced and the mixture was agitated for 10 minutes at 25° C. Next, the mixture was filtered and washed with 255 ml of deionized water and 142 ml of methanol. The obtained solids were dried to obtain 8.4 g of target di-t-butyl crotyl phosphonium tetraphenyl borate as white solids. The yield was 42%.

1H-NMR spectrum (DMSO-d6) δ ppm: 1.40, 1.42 (d, J=16.5 Hz, 18H, (CH$_3$C)$_2$—P— (cis isomer+trans isomer)), 1.67-1.73 (m, 3H, —CH=CH—CH$_3$(cis isomer+trans isomer)), 3.33 (br-s, 2H (CH$_3$C)$_2$P—CH$_2$— (cis isomer+trans isomer)), 5.48-5.54 (m, 1H, —CH=CH—CH$_3$ (cis isomer+trans isomer)), 5.75-5.92 (m, 1H, —CH=CH—CH$_3$ (cis isomer +trans isomer)), 6.78 (t, J=7.10 Hz, 4H, B—Ph (cis isomer+trans isomer)), 6.92 (t, 8H, J=7.56 Hz, B-Ph (cis isomer+trans isomer)), 7.15-7.19 (m, 8H, B-$\vec{Ph}$ (cis isomer+ trans isomer))

Melting point: 169° C.

Example 5

Manufacture of Bis(Di-t-Butyl Prenyl Phosphine) Palladium Dichloride 5.3 ml of tetrahydrofuran, 5.5 ml of toluene, 9.5 g (0.050 mol) of di-t-butyl phosphinous chloride, and 0.15 g (0.0015 mol (corresponding to 3 percent by mol)) of copper (I) chloride were introduced to a fully nitrogen-replaced four-neck flask of 100 ml in capacity. Into this flask, a Grignard reagent solution prepared in advance from 5.8 g (0.055 mol) of prenyl chloride and 2.7 g (0.11 mol) of metal magnesium in 119 ml of tetrahydrofuran was dripped over 1 hour by maintaining temperatures between 30° C. and 40° C. When the dripping was completed, the mixture was agitated for 1 hour at temperatures between 30° C. and 40° C. The reaction liquid was returned to 25° C., and then loss of di-t-butyl phosphinous chloride was checked by gas chromatography. Thereafter, 8 ml of 3% aqueous solution of sulfuric acid was added to the reaction liquid to separate the organic layer, which was then washed in water. Next, 56 ml of 10% aqueous solution of sulfuric acid was added and the mixture was agitated for 30 minutes and then separated. The bottom layer was washed with 6 ml of toluene, after which 29 ml of hexane and 20 ml of 20% aqueous solution of sodium hydroxide were added and the mixture was agitated for 30 minutes and separated. The top layer was washed in water, 45.9 g (0.012 mol) of methanol solution of sodium tetrachloropalladate (II) was introduced, and the mixture was heated to reflux for 10 minutes. Next, the mixture was cooled to 25° C., filtered, and washed with 29 ml of methanol. The obtained solids were dried to obtain 6.1 g of target bis(di-t-butyl prenyl phosphine) palladium dichloride as yellow solids (yield 41%).

1H-NMR spectrum (CDCl$_3$) δ ppm: 1.47 (d, J=6.8 Hz, 9H, (CH$_3$C)$_2$—P—), 1.49 (d, J=6.8 Hz, 9H (CH$_3$C)$_2$—P—), 1.63 (s, 3H, —CH=CCH$_3$(CH$_3$)), 1.74 (s, 3H, —CH=CCH$_3$ (CH$_3$)), 2.82 (br-s, 2H, (CH$_3$C)$_2$P—CH$_2$—), 5.57 (br-s, 1H, —CH=C (CH$_3$)$_2$)

Melting point: 213'C (Breakdown occurred)

Example 6

Manufacture of bis(dicyclohexyl prenyl phosphine) palladium dichloride

Reaction was caused according to the same method as in Example 5, except that dicyclohexyl phosphinous chloride was used instead of di-t-butyl phosphinous chloride, and as a result of which 7.5 g of target bis(dicyclohexyl prenyl phosphine) palladium dichloride was obtained as yellow solids (yield 44%).

1H-NMR spectrum (CDCl$_3$) δ ppm: 1.14-1.32 (m, 6H), 1.57-1.72 (m, 6H), 1.67 (s, 3H, —CH$_2$CH═C (CH$_3$)$_2$), 1.72 (s, 3H, —CH$_2$CH═C (CH$_3$)$_2$), 1.79-1.84 (m, 6H), 2.04 (br-d, 12.4 Hz, 2.15 (m, 2H), 2.79 (br-s, 2H, P—CH$_2$—CH═C (CH$_3$)$_2$), 5.33 (br-s, 1H, —CH═C (CH$_3$)$_2$)

Melting point: 193° C. (Breakdown occurred)

Comparative Example 1

Synthesis of N,N'-bis(1,3-dimethyl phenyl)-N,N'-diphenyl-1,4-phenylene diamine from N,N'-diphenyl phenylene diamine and 2-chloro-1,3-dimethyl benzene In an inert gas ambience, N,N'-diphenyl phenylene diamine (10 mmol), 2-chloro-1,3-dimethyl benzene (22 mmol), palladium acetate (0.1 mmol), di-t-butyl phenyl phosphine (0.2 mmol), sodium t-butoxide (30 mmol), and o-xylene (40 mL) were agitated for 6 hours at 130 to 135° C., and when the obtained reaction mixture was quantified by HPLC using an internal standard substance, the target N,N'-bis(1,3-dimethyl phenyl)-N,N'-diphenyl-1,4-phenylene diamine was obtained at a yield of 46%. (a retest from Patent Literature 2)

Example 7

Reaction was caused under the same conditions as in Comparative Example 1, except that bis(di-t-butyl crotyl phosphine) palladium dichloride (0.1 mmol) was used instead of di-t-butyl phenyl phosphine and palladium acetate, and as a result of which the target N,N'-bis(1,3-dimetyl phenyl)-N,N'-diphenyl-1,4-phenylene diamine was obtained at a yield of 82%. Clearly, the manufacturing method proposed by the present invention allowed the target substance to be obtained at a higher yield than when the manufacturing method in Comparative Example 1 (a retest from Patent Literature 2) was used.

Comparative Example 2

Synthesis of 2,6-dimethyl-N,N-diphenyl aniline from N,N-diphenyl amine and 2-chloro-1,3-dimethyl benzene In an inert gas ambience, N,N-diphenyl amine (2.0 mmol), 2-chloro-1,3-dimethyl benzene (3.0 mmol), bis(di-t-butyl aryl phosphine) palladium dichloride (0.01 mmol), sodium t-butoxide (3.6 mmol), and o-xylene (4 mL) were agitated for 6 hours at 145° C., and when the obtained reaction mixture was quantified by HPLC using an internal standard substance, the target 2,6-dimethyl-N,N-diphenyl aniline was obtained at a yield of 29%.

Example 8

Reaction was caused under the same conditions as in Comparative Example 2, except that bis(di-t-butyl prenyl phosphine) palladium dichloride (0.01 mmol) was used instead of bis(di-t-butyl aryl phosphine) palladium dichloride, and as a result of which the target 2,6-dimethyl-N,N-diphenyl aniline was obtained at a yield of 68%. Clearly, the manufacturing method proposed by the present invention allowed the target substance to be obtained at a higher yield than when the manufacturing method in Comparative Example 2 was used.

Comparative Example 3

Synthesis of (N-chlorophenyl)-2,4,6-trimethyl aniline from 2,4,6-trimethyl aniline and 1-bromo-2-chlorobenzene In an inert gas ambience, 2,4,6-trimethyl aniline (10.0 mmol), 1-bromo-2-chlorobenzene (10.0 mmol), bis(tri-t-butyl phosphine) palladium (0.01 mmol), sodium t-butoxide (12.0 mmol), and o-xylene (20 mL) were agitated for 6 hours at 140° C. When the reaction mixture was analyzed by GC, the target (N-chlorophenyl)-2,4,6-trimethyl aniline was obtained at a yield of 31%.

Comparative Example 4

Reaction was caused under the same conditions as in Comparative Example 3, except that palladium chloride (0.01 mmol) and di-t-butyl(4-dimethyl aminophenyl)phosphine (0.02 mmol) were used instead of bis(tri-t-butyl phosphine) palladium, and as a result of which the target (N-chlorophenyl)-2,4,6-trimethyl aniline was obtained at a yield of 70%.

Example 9

Reaction was caused under the same conditions as in Comparative Example 3, except that bis(di-t-butyl crotyl phosphine) palladium dichloride (0.01 mmol) was used instead of bis(tri-t-butyl phosphine) palladium, and as a result of which the target (N-chlorophenyl)-2,4,6-trimethyl aniline was obtained at a yield of 94%. Clearly, the manufacturing method proposed by the present invention allowed the target substance to be obtained at a higher yield than when the manufacturing method in Comparative Example 3 or 4 was used.

Comparative Example 5

Synthesis of 2,4',6-trimethyl biphenyl from 2-chloro-1,3-dimethyl benzene and 4-methyl phenyl boronate anhydride In an inert gas ambience, 2-chloro-1,3-dimethyl benzene (10 mmol), 4-methyl phenyl boronate anhydride (5 mmol), palladium chloride (0.1 mmol), di-t-butyl(4-dimethyl aminophenyl)phosphine (0.2 mmol), potassium carbonate (20 mmol), 1,4-dioxane (27 mL), and water (3 mL) were agitated for 5 hours at 80° C. When the reaction mixture was analyzed by GC, the target 2,4',6-trimethyl biphenyl was obtained at a yield of 84%. (a retest from Non-patent Literature 1)

Comparative Example 6

Reaction was caused under the same conditions as in Comparative Example 5, except that bis(tri-t-butyl phosphine) palladium (0.1 mmol) was used instead of di-t-butyl (4-dimethyl aminophenyl)phosphine and palladium chloride, and as a result of which the target 2,4',6-trimethyl biphenyl was obtained at a yield of 60%.

Example 10

Reaction was caused under the same conditions as in Comparative Example 5, except that bis(di-t-butyl crotyl phosphine) palladium dichloride (0.1 mmol) was used instead of di-t-butyl(4-dimethyl aminophenyl)phosphine and palladium chloride, and the reaction time was three hours, and as a result of which the target 2,4',6-trimethyl biphenyl was obtained at a yield of 91%. Clearly, the manufacturing method proposed by the present invention allowed the target substance to be obtained with a shorter reaction time and at a higher yield than when the manufacturing method in Comparative Example 5 (a retest from Non-patent Literature 1) or 6 was used.

Example 11

Reaction was caused under the same conditions as in Comparative Example 5, except that di-t-butyl crotyl phosphonium tetrafuloroborate (0.20 mmol) and bis(dibenzylidene acetone) palladium (0.10 mmol) were used instead of bis(di-t-butyl crotyl phosphine) palladium dichloride, and as a result of which the target 2-methoxy-4'-methyl biphenyl was obtained at a yield of 92%.

Comparative Example 7

Synthesis of 2-methoxy-4'-methyl biphenyl from 2-chloroanisole and 4-methyl phenyl boronate anhydride In an inert gas ambience, 2-chloroanisole (10 mmol), 4-methyl phenyl boronate anhydride (7 mmol), bis(tri-t-butyl phosphine) palladium (0.05 mmol), potassium phosphate (15 mmol), 1,4-dioxane (18 mL), and water (2 mL) were agitated for 2 hours at 100° C. When the reaction mixture was analyzed by GC, the target 2-methoxy-4'-methyl biphenyl was obtained at a yield of 72%.

Comparative Example 8

Reaction was caused under the same conditions as in Comparative Example 7, except that palladium chloride (0.05 mmol) and di-t-butyl(4-dimethyl aminophenyl) phosphine (0.1 mmol) were used instead of bis(tri-t-butyl phosphine) palladium, and as a result of which the target 2-methoxy-4'-methyl biphenyl was obtained at a yield of 78%.

Comparative Example 9

Reaction was caused under the same conditions as in Comparative Example 7, except that palladium acetate (0.05 mmol) and di-t-butyl-n-butyl phosphine (0.10 mmol) were used instead of bis(tri-t-butyl phosphine) palladium, and as a result of which the target 2-methoxy-4'-methyl biphenyl was obtained at a yield of 75%.

Example 12

Reaction was caused under the same conditions as in Comparative Example 7, except that bis(di-t-butyl prenyl phosphine) palladium dichloride (0.05 mmol) was used instead of bis(tri-t-butyl phosphine) palladium, and as a result of which the target 2-methoxy-4'-methyl biphenyl was obtained at a yield of 93%. Clearly, the manufacturing method proposed by the present invention allowed the target substance to be obtained at a higher yield than when the manufacturing method in any of Comparative Examples 7 to 9 was used.

Comparative Example 10

Synthesis of 2-ethenyl methoxy benzene from 2-bromoanisole and vinyl boronate anhydride-pyridine complex In an inert gas ambience, 2-bromoanisole (10 mmol), vinyl boronate anhydride-pyridine complex (4 mmol), bis (tri-t-butyl phosphine) palladium (0.05 mmol), potassium phosphate (15 mmol), 1,4-dioxane (18 mL), and water (2 mL) were agitated for 6 hours at 80° C. When the reaction mixture was analyzed by GC, the target 2-ethenyl methoxy benzene was obtained at a yield of 54%.

Example 13

Reaction was caused under the same conditions as in Comparative Example 10, except that bis(di-t-butyl crotyl phosphine) palladium dichloride (0.05 mmol) was used instead of bis(tri-t-butyl phosphine) palladium, and as a result of which the target 2-ethenyl methoxy benzene was obtained at a yield of 87%. Clearly, the manufacturing method proposed by the present invention allowed the target substance to be obtained at a higher yield than when the manufacturing method in Comparative Example 10 was used.

Comparative Example 11

Synthesis of 9-(3-chlorophenyl)-9H-carbazole from 1-bromo-3-chlorobenzene and carbazole In an inert gas ambience, carbazole (10 mmol), 1-bromo-3-chlorobenzene (11 mmol), bis(di-t-butyl phenyl phosphine) palladium dichloride (0.3 mmol), sodium t-butoxide (15 mmol), and o-xylene (80 mL) were agitated for 9 hours at 135° C., and when the obtained reaction mixture was quantified by GC using an internal standard substance, the target 9-(3-chlorophenyl)-9H-carbazole was obtained at a yield of 67%.

Example 14

Reaction was caused under the same conditions as in Comparative Example 11, except that bis(di-t-butyl crotyl phosphine) palladium dichloride (0.3 mmol) was used instead of bis(di-t-butyl phenyl phosphine) palladium dichloride, and as a result of which the target 9-(3-chlorophenyl)-9H-carbazole was obtained at a yield of 95%. Clearly, the manufacturing method proposed by the present invention allowed the target substance to be obtained at a higher yield than when the manufacturing method in Comparative Example 11 was used.

Example 15

Synthesis of 4-tolyl morpholine from 2-chlorotoluene and morpholine

In an inert gas ambience, 2-chlorotoluene (10 mmol), morpholine (12 mmol), bis(di-t-butyl crotyl phosphine) palladium dichloride (0.01 mmol), sodium t-butoxide (12 mmol), and o-xylene (20 mL) were agitated for 6 hours at 135° C., and when the obtained reaction mixture was analyzed by GC, the target 4-tolyl morpholine was obtained at a yield of 58%.

Example 16

Synthesis of 4'-methyl biphenyl-4-carbonitrile from 4-chlorobenzonitrile and 4-methy phenyl boronate anhydride In an inert gas ambience, 4-chlorobenzonitrile (10 mmol), 4-methyl phenyl boronate anhydride (7 mmol), bis(1,5-cyclooctadiene) nickel (0.5 mmol), di-t-butyl crotyl phosphine (1.0 mmol), potassium phosphate (15 mmol), 1,4-dioxane (18 mL), and water (2 mL) were agitated for 6 hours at 80° C. When the reaction mixture was analyzed by GC, the target 4'-methyl biphenyl-4-carbonitrile was obtained at a yield of 88%.

What is claimed is:

1. A phosphine compound expressed by General Formula (1) below:

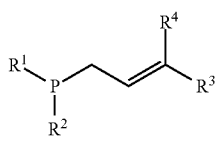

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, aromatic group, alicyclic group, or heterocyclic group; note that $R^3$ and $R^4$ have no phosphorus atom and that $R^3$ and $R^4$ are not both hydrogen at the same time).

2. A phosphine compound expressed by General Formula (1) below:

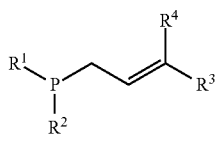

(1)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group; note that $R^3$ and $R^4$ have no phosphorus atom and that $R^3$ and $R^4$ are not both hydrogen at the same time), wherein $R^1$ and $R^2$ are both a t-butyl group in General Formula (1).

3. A phosphine compound according to claim 2, expressed by Formula (2) below:

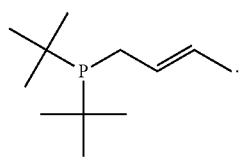

(2)

4. A phosphine compound according to claim 2, expressed by Formula (3) below:

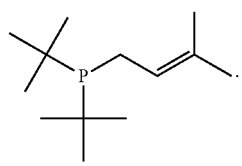

(3)

5. A phosphonium salt compound expressed by General Formula (6) below:

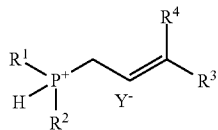

(6)

(In the formula, $R^1$ and $R^2$ are each independently a secondary alkyl group, tertiary alkyl group, or cycloalkyl group, while $R^3$ and $R^4$ are each independently a hydrogen, aliphatic group, heteroaliphatic group, aromatic group, alicyclic group, or heterocyclic group, and $Y^-$ represents $B^-F_4$ or $B^-Ph_4$; note that $R^3$ and $R^4$ have no phosphorus atom and that $R^3$ and $R^4$ are not both hydrogen at the same time).

6. A phosphonium salt compound according to claim 5, wherein $R^1$ and $R^2$ are each a tertiary butyl group in Formula (6).

* * * * *